United States Patent
Snacken et al.

(10) Patent No.: US 11,320,358 B2
(45) Date of Patent: May 3, 2022

(54) METHOD, A SYSTEM, AND A COMPUTER PROGRAM PRODUCT FOR DETERMINING SOIL PROPERTIES USING PUMPING TESTS

(71) Applicant: Fugro N.V., Leidschendam (NL)

(72) Inventors: Barbara Snacken, Leidschendam (NL); Bastiaan Martinus Berbee, Leidschendam (NL)

(73) Assignee: FUGRO N.V.

( * ) Notice: Subject to any disclaimer, the term of this patent is extended or adjusted under 35 U.S.C. 154(b) by 102 days.

(21) Appl. No.: 16/310,362

(22) PCT Filed: Jun. 20, 2017

(86) PCT No.: PCT/NL2017/050410
§ 371 (c)(1),
(2) Date: Dec. 14, 2018

(87) PCT Pub. No.: WO2017/222372
PCT Pub. Date: Dec. 28, 2017

(65) Prior Publication Data
US 2019/0250090 A1    Aug. 15, 2019

(30) Foreign Application Priority Data
Jun. 20, 2016 (NL) .................................. 2017006

(51) Int. Cl.
*G01N 15/08* (2006.01)
*E02D 1/02* (2006.01)
(Continued)

(52) U.S. Cl.
CPC ......... *G01N 15/0826* (2013.01); *E02D 1/027* (2013.01); *E02D 1/04* (2013.01);
(Continued)

(58) Field of Classification Search
CPC .... G01N 15/0826; E21B 47/008; E21B 47/06
(Continued)

(56) References Cited

U.S. PATENT DOCUMENTS

| | | | | | |
|---|---|---|---|---|---|
| 4,192,182 | A | * | 3/1980 | Sylvester | ................ E21B 43/17 166/271 |
| 4,228,855 | A | * | 10/1980 | Sustek, Jr. | ............... E21B 47/11 166/250.03 |

(Continued)

FOREIGN PATENT DOCUMENTS

| WO | 2010129677 A2 | 11/2010 |
|---|---|---|
| WO | 2017222372 A1 | 12/2017 |

OTHER PUBLICATIONS

International Search Report and Written Opinion; PCT Application No. PCT/NL2017/050410; dated Aug. 9, 2017.
(Continued)

*Primary Examiner* — Tran M. Tran
(74) *Attorney, Agent, or Firm* — Polsinelli PC

(57) ABSTRACT

A method, system and computer program product for determining soil properties comprising a probe including at least a liquid injection port and a pressure transducer. The probe is pushed into a soil and one or more pumping tests are carried out, wherein during a pumping test infiltration liquid is pumped through the liquid injection port of the probe. By means of the pressure transducer a pressure response in the soil resulting from the injection of liquid through the liquid injection port is measured for each of the one or more pumping tests.

29 Claims, 9 Drawing Sheets

(51) Int. Cl.
  *E21B 49/00* (2006.01)
  *E21B 7/20* (2006.01)
  *E02D 1/04* (2006.01)
  *G01N 33/24* (2006.01)

(52) U.S. Cl.
  CPC ............. *E21B 7/20* (2013.01); *E21B 49/008* (2013.01); *G01N 33/24* (2013.01)

(58) Field of Classification Search
  USPC .............. 73/152.05, 152.16, 152.22, 152.39, 73/152.41
  See application file for complete search history.

(56) References Cited

U.S. PATENT DOCUMENTS

| | | | | |
|---|---|---|---|---|
| 4,352,780 A * | 10/1982 | Schick | ................ | G01N 35/085 422/63 |
| 4,353,249 A * | 10/1982 | Lagus | ................ | E21B 47/11 73/152.41 |
| 4,400,970 A * | 8/1983 | Ali | ................ | E02D 1/022 73/84 |
| 4,420,975 A * | 12/1983 | Nagel | ................ | E21B 49/008 73/152.05 |
| 4,453,401 A * | 6/1984 | Sidey | ................ | G01L 9/0001 73/73 |
| 4,492,111 A * | 1/1985 | Kirkland | ................ | G01N 3/48 324/323 |
| 4,523,459 A * | 6/1985 | Hastings | ................ | E21B 47/10 166/271 |
| 4,554,819 A * | 11/1985 | Ali | ................ | G01N 3/00 73/9 |
| 4,742,459 A * | 5/1988 | Lasseter | ................ | E21B 49/008 166/100 |
| 4,799,157 A * | 1/1989 | Kucuk | ................ | E21B 49/008 702/12 |
| 4,807,707 A * | 2/1989 | Handley | ................ | E21B 7/26 175/20 |
| 4,856,318 A * | 8/1989 | Hogan | ................ | G01N 3/303 73/12.13 |
| 4,860,581 A * | 8/1989 | Zimmerman | ................ | E21B 49/10 73/152.26 |
| 4,936,139 A * | 6/1990 | Zimmerman | ................ | E21B 49/08 175/40 |
| 5,042,595 A * | 8/1991 | Ladanyi | ................ | E21B 49/006 175/50 |
| 5,168,765 A * | 12/1992 | Broussard | ................ | E21B 7/26 175/21 |
| 5,219,388 A * | 6/1993 | Meletiou | ................ | E21B 49/008 73/152.31 |
| 5,335,542 A * | 8/1994 | Ramakrishnan | .... | E21B 33/1246 166/250.02 |
| 5,520,248 A * | 5/1996 | Sisson | ................ | E21B 33/1243 166/250.02 |
| 5,888,021 A * | 3/1999 | Kawabata | ................ | B09C 1/00 166/246 |
| 6,002,063 A * | 12/1999 | Bilak | ................ | B09B 1/00 588/17 |
| 6,061,634 A * | 5/2000 | Belani | ................ | E21B 49/008 702/12 |
| 6,098,448 A * | 8/2000 | Lowry | ................ | G01N 15/08 175/21 |
| H2052 H * | 12/2002 | Molz, III | ................ | 702/12 |
| 6,575,244 B2 * | 6/2003 | Chang | ................ | E21B 21/08 166/250.15 |
| 6,672,386 B2 * | 1/2004 | Krueger | ................ | E21B 49/008 166/252.5 |
| 6,772,621 B2 * | 8/2004 | Grover | ................ | G01N 19/10 137/78.2 |
| 6,843,119 B2 * | 1/2005 | Patey | ................ | E21B 17/028 73/152.18 |
| 7,059,174 B2 * | 6/2006 | Ranjan | ................ | E21B 49/008 73/38 |
| 7,117,734 B2 * | 10/2006 | Follini | ................ | E21B 47/10 73/152.41 |
| 7,234,362 B2 * | 6/2007 | Shinn, II | ................ | G01N 33/24 73/784 |
| 7,234,521 B2 * | 6/2007 | Shammai | ................ | E21B 49/008 166/264 |
| 7,272,973 B2 * | 9/2007 | Craig | ................ | E21B 49/008 73/200 |
| 7,281,422 B2 * | 10/2007 | Keller | ................ | E21B 43/103 166/250.03 |
| 7,281,588 B2 * | 10/2007 | Shampine | ................ | E21B 19/22 166/382 |
| 7,313,481 B2 * | 12/2007 | Moos | ................ | E21B 43/00 702/12 |
| 7,425,307 B2 * | 9/2008 | Sohl, III | ................ | E02D 1/02 250/253 |
| 7,659,123 B2 * | 2/2010 | Ball | ................ | G01N 15/0826 422/50 |
| 7,886,591 B2 * | 2/2011 | Ramakrishnan | ......... | G01V 3/20 702/12 |
| 7,971,649 B2 * | 7/2011 | Zupanick | ............ | F04C 15/0065 166/50 |
| 8,087,292 B2 * | 1/2012 | Voelker | ................ | E21B 49/008 73/152.41 |
| 8,191,416 B2 * | 6/2012 | Kuchuk | ................ | E21B 49/008 73/152.41 |
| 8,210,036 B2 * | 7/2012 | Bekkeheien | .......... | E21B 49/008 73/152.51 |
| 8,794,318 B2 * | 8/2014 | Harrigan | ................ | E21B 49/008 166/100 |
| 8,839,668 B2 * | 9/2014 | Hemsing | ................ | E21B 49/008 73/152.27 |
| 8,955,375 B2 * | 2/2015 | DiFoggio | .............. | E21B 49/081 73/152.28 |
| 8,991,245 B2 * | 3/2015 | Fields | ................ | E21B 7/061 73/152.41 |
| 9,140,615 B2 * | 9/2015 | Kia | ................ | G01L 1/242 |
| 9,284,707 B2 * | 3/2016 | Barron | ................ | E02D 3/12 |
| 9,371,710 B2 * | 6/2016 | Ramakrishnan | ...... | E21B 49/008 |
| 9,435,188 B2 * | 9/2016 | Gray | ................ | E21B 47/00 |
| 9,790,788 B2 * | 10/2017 | Moos | ................ | E21B 43/25 |
| 9,938,785 B2 * | 4/2018 | Gleitman | ................ | E21B 17/028 |
| 10,132,159 B2 * | 11/2018 | Burgos | ................ | E21B 47/06 |
| 10,215,002 B2 * | 2/2019 | Al-Hajri | ................ | E21B 47/10 |
| 10,385,670 B2 * | 8/2019 | James | ................ | E21B 43/26 |
| 10,385,686 B2 * | 8/2019 | James | ................ | E21B 43/26 |
| 10,458,207 B1 * | 10/2019 | Matringe | ................ | E21B 47/11 |
| 10,480,302 B2 * | 11/2019 | Irani | ................ | E21B 7/007 |
| 10,494,921 B2 * | 12/2019 | Weng | ................ | E21B 47/09 |
| 10,591,636 B2 * | 3/2020 | Willerth | ................ | E21B 47/024 |
| 10,655,461 B2 * | 5/2020 | Pinto | ................ | E21B 47/06 |
| 10,697,876 B1 * | 6/2020 | Jamison | ................ | B81B 7/02 |
| 10,920,570 B2 * | 2/2021 | Jamison | ................ | E21B 44/04 |
| 11,150,155 B2 * | 10/2021 | Pool | ................ | G01L 7/00 |
| 11,231,350 B2 * | 1/2022 | Karabacak | ............ | G01N 3/068 |
| 2008/0230221 A1 * | 9/2008 | Zafari | ................ | E21B 49/087 166/254.1 |
| 2009/0107725 A1 * | 4/2009 | Christy | ................ | E21B 49/083 175/50 |
| 2010/0257920 A1 * | 10/2010 | Lee | ................ | E02D 1/022 73/84 |
| 2017/0233968 A1 * | 8/2017 | Cai | ................ | G01L 23/26 73/170.32 |
| 2017/0370064 A1 * | 12/2017 | Morgan | ................ | G01J 3/108 |
| 2018/0252629 A1 * | 9/2018 | Zumbroich | ............ | G01N 33/24 |

OTHER PUBLICATIONS www.fugro.com et al., "Fugro HPT-CPT Probe", Mar. 4, 2016; pp. 1-2, XP055356533; retrieved from www.fugro.com on Mar. 20, 2017.

(56) References Cited

OTHER PUBLICATIONS

Doug Koehler et al.,"Welcome to Our Webinar: Using Hydraulic Profiling Tool (HPT) Logs for Site Characterization", Mar. 4, 2013; pp. 1-81, XP055356592; retrieved from URL: http://files.geoprobe.com/pdfs/hpt_webinar_mod1_0.pdf on Mar. 20, 2017.

* cited by examiner

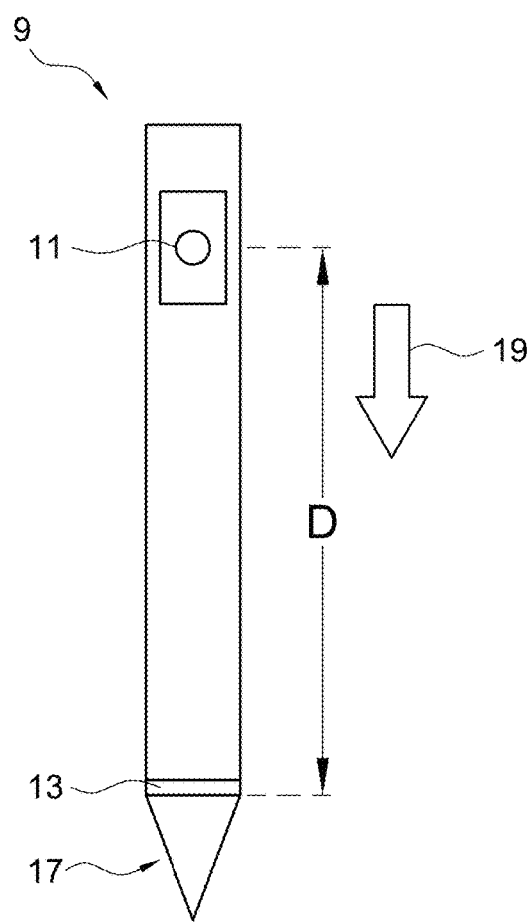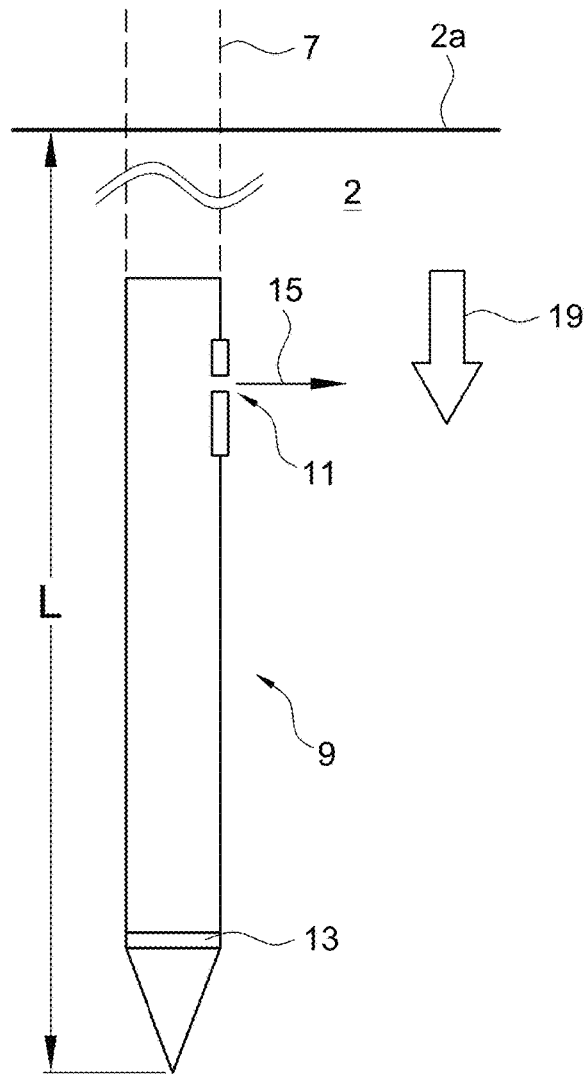
Fig. 3A
Fig. 3B

METHOD, A SYSTEM, AND A COMPUTER PROGRAM PRODUCT FOR DETERMINING SOIL PROPERTIES USING PUMPING TESTS

CROSS-REFERENCE TO RELATED APPLICATIONS

This application is a national stage application of International Application No. PCT/NL2017/050410, which was filed on Jun. 20, 2017, which claims priority to Netherlands Application Number 2017006 filed on Jun. 20, 2016, of which is incorporated by reference in its entirety.

FIELD OF THE INVENTION

The invention relates to a method and system for determining soil properties by use of pumping tests. In particular, the present invention relates to a pumping test that has enhanced results and requires less time and power.

In the context of the present invention, it should be understood that a pumping test is a test that is carried out either by injecting or extracting water from the soil. For ease of explanation, the present invention is described in terms of liquid injection; however, a skilled person would easily understand that similar principles apply to liquid extraction.

BACKGROUND OF THE INVENTION

An aquifer is a geological unit sufficiently permeable to yield quantities of water to wells. Aquifers can be classified in categories such as confined aquifers, unconfined aquifers, leaky aquifers. The most common aquifers are unconsolidated sand and gravels, but permeable sedimentary rocks such as sandstone and limestone, and heavily fractured or weathered volcanic and crystalline rocks can also be classified as aquifers.

A classic pumping test is commonly employed to determine hydro-geological parameters and/or characterize a system of aquifers, aquitards and flow system boundaries. An aquifer can be evaluated and the characteristics of the aquifer (e.g. hydraulic conductivity, permeability, storativity, etc.) can be quantified by conducting a pumping test. The effect of constant pumping of a liquid is analyzed by observation of the response or result on the aquifer in the form of a drawdown in observation wells. Typically, a classic pumping test is conducted by pumping water from one extraction well at a constant rate and for an extended period of time of at least one day (usually multiple days), while simultaneously measuring the water levels in nearby observation wells prior to, during and after pumping. The data can then be used to obtain resulting drawdown and recovery curves. The hydraulic pressure surrounding the well in the aquifer that feeds the well declines as a result of water being pumped from the extraction well. This will show up as drawdown in observation wells. The drawdown will increase with the duration of pumping and decrease with radial distance from the extractionwell. As the discharge of the extraction well and drawdown in the observation wells at known distances from the extraction well are measured, the measurements can be substituted into an appropriate equation for calculating the hydraulic characteristics of the aquifer. Analytical models and/or numerical models of aquifer flow can be utilized to analyze the results of a pumping test.

Classic pumping tests can last for days or even weeks in duration, depending on the purpose of the pumping test. Alternatively, a quick estimate of the aquifer properties immediately around a well can be obtained by employing a slug test, wherein the effects of an induced instantaneous change (increase or decrease) in the same well are observed. Compared to a typical pumping test, a slug test can be performed within the range of minutes instead of days. However, the results from a slug test are less accurate when it comes to characterization of a whole aquifer.

Furthermore, classic pumping tests can be quite sensitive to measurement errors, which can make the measurements relatively demanding for obtaining accurate results. It is important to accurately record the data. The water levels, time of the measurements and pumping rates must be carefully recorded and checked. In the classic pumping test the measurement comprises the entire aquifer and cannot be limited to limited parts of the aquifer. So the resolution of the measurement is limited.

Also, different types of aquifers can exhibit similar drawdown behaviors, which demand experience and interpretational skills on the part of the engineer or geologist for finding reliable values for the hydraulic characteristics of the geological formations through which the groundwater is moving.

Furthermore, the relatively large volume of pumped water during a pumping test needs to be discharged properly so as to ensure that there is no damage due to erosion, flooding, sediment deposits in streams, etcetera.

Therefore, classic pumping tests commonly result in high costs and require much resources. They are time consuming and also may fail to provide insight in detailed layering of a geohydrological aquifer.

SUMMARY OF THE INVENTION

It is an object of the invention to provide for a method and a system that obviates at least one of the above mentioned drawbacks, while maintaining the advantages.

The method for determining soil properties comprises pushing a probe system, including at least one liquid injection port and at least one pressure transducer, into a soil; carrying out one or more pumping tests, wherein during a pumping test an infiltration liquid is pumped through the liquid injection port into the soil; and measuring by means of at least one pressure transducer of the probe, for each of the pumping tests, a pressure response of the soil resulting from the injection of liquid into the soil, e.g., through the liquid injection port. In this way, also the pore water pressure resulting from the liquid injection can be determined. The infiltration liquid can include ground water. Alternatively, or additionally, the infiltration liquid can include foreign water or a non-water liquid. The permeability and storativity of a soil can be determined by use of the measured values, e.g. by fitting the measured values on a computational model. The one or more pumping tests can be seen as a liquid injection test, in which liquid is injected rather than extracted as in classic pumping tests. Instead of injecting liquid and observing a pressure response by a probe, during such a classic pumping test the drop in hydraulic head pressure or pore water pressure in the surrounding area is registered by looking at water levels in surrounding monitoring wells.

Optionally, the probe system includes a probe having a substantially elongated tubular shape comprising a tip facing in a longitudinal penetration direction of the probe and arranged for penetrating the soil. The probe can include at least one liquid injection port and at least one pressure transducer.

Optionally, the liquid injection port and the pressure transducer are arranged at a distance from each other.

Optionally, the liquid injection port and the pressure transducer are arranged at a distance from each other with respect to a longitudinal direction of the probe. Optionally the probe includes a plurality of pressure transducers at longitudinal distances along the probe.

Optionally, the liquid injection port and at least one pressure transducer are arranged at a distance from each other with respect to a lateral direction of a probe of the probe system.

Optionally the pumping test can be combined with one or more pressure transducers in the 3D space (X, Y, Z) around the injection point. The probe system can include a first probe including at least one liquid injection port. The probe system can include a second probe including at least one pressure transducer. Additional pressure transducers could be placed using one or more additional probes.

Optionally the one or more pressure transducers in the 3D space around the injection point could be used to derive horizontal and/or vertical permeability and storativity from the measured pressure response on the injected liquid Q.

Optionally the horizontal and/or vertical permeability and storativity can be derived using numerical or analytical calculations with an inverse modelling technique.

Optionally, the one or more pumping tests are carried out at a substantially fixed depth of soil penetration of the probe system. The penetration depth of the probe system can be defined as the penetration depth of the probe or the penetration depth of the first probe. During a method for determining soil properties according to the present invention, the probe(s) can be pushed into the soil until a certain depth of penetration of the probe(s) is reached. The movement of the probe(s) can be stopped at a depth where one or more pumping tests are to be conducted. The depth of penetration of the probe(s) which can correspond to a depth of the probe(s) relative to the soil surface, can be set manually or automatically. For instance, a controller may comprise preset depth data or settings, which may be adjustable or configurable. Also, an operator can configure the depth data via an interface such as e.g. a monitor connected to a digital computer. Optionally, a plurality of measurement penetration depths are possible in a measurement campaign, wherein measurements are conducted at certain depths or depth increments.

Optionally, the one or more pumping tests are carried out at a substantially constant liquid injection flow rate Q. The liquid injection flow rate Q through the liquid injection port can be controlled and/or adjustable. During a pumping test the liquid injection flow rate Q can be controlled in such a way so as to obtain a substantially constant liquid injection flow rate Q.

Optionally, the one or more pumping tests comprise a plurality of successive pumping tests carried out at a different liquid injection flow rates Q. When the one or more pumping tests comprise a plurality of different pumping tests, the liquid injection flow rate Q for the different pumping tests can also be different. Optionally, the liquid injection flow rate Q for each of the pumping tests is kept at a substantially constant value, while the successive pumping tests are carried out at a different liquid injection flow rate Q compared to at least another pumping test of the one or more pumping tests. Optionally, for example at a certain depth of penetration where one or more pumping tests are carried out, all the pumping tests of the one or more pumping tests have different liquid injection flow rates Q with respect to each other. The one or more pumping tests may be performed without delay time between the successive pumping tests. The pumping tests may constitute a continuous series of pumping tests in which the liquid injection flow rate is changed, e.g. stepwise. The continuous series of pumping tests of stepwise increasing injection flow rate is herein also referred to as steptest. Optionally, some pumping tests of the one or more pumping tests at a certain fixed pumping test depth of penetration, have a same liquid injection flow rate Q, while other pumping tests of the one or more pumping tests have different liquid injection flow rates Q. Optionally, the time between successive pumping tests can be set. Hence a series of individual pumping tests with periods of rest, i.e. no liquid injection, in between can be provided. Such a timing can influence the accuracy of the measurements using the one or more pumping tests.

Optionally, one or more pumping tests are carried out starting from a substantially hydrostatic pressure state. The one or more pumping tests can be regarded as injection tests. Optionally, prior to conducting one or more pumping tests, a hydrostatic state is obtained, e.g. by dissipation of the pressure. The pressure increase at the pressure transducer of the probe can be measured as a result of a stepwise adjustment of the injection flow rate Q at the point of infiltration, i.e. liquid injection at the injection port of the probe. Optionally, the stepwise adjustment of the injection flow rate Q is a stepwise pressure increase. A pressure response can be obtained by measuring the pressure at the pressure transducer of the probe. Optionally, the pressure transducer is located at a position adjacent a tip and/or cone of the probe.

Optionally, the method further comprises carrying out at least one dissipation test, wherein pumping of infiltration liquid through the liquid injection port of the probe is stopped in order to obtain a substantially hydrostatic pressure state. During a dissipation test the pumping can be stopped. In this way, excess pressure can decay with time during a dissipation test and eventually reach substantially equilibrium conditions corresponding to hydrostatic values.

Optionally, a dissipation test is carried out prior to starting the one or more pumping tests. By conducting the one or more pumping tests after performing a dissipation test, the one or more pumping tests can start from a substantially hydrostatic pressure state.

Optionally, a successive pumping test is carried out when the pressure response during a previous pumping test has converged to a substantially constant value. The substantially constant value can be reached after a certain amount of time. In some examples the substantially constant value can be assumed to be reached after a period of five minutes. During a pumping test wherein liquid is injected in the soil through the liquid injection port of the probe, an equilibrium condition can be reached in time. Optionally, the liquid injection flow rate Q during a pumping test is kept constant while the probe is kept at a fixed depth, allowing to obtain an equilibrium condition in time, wherein the pressure measured by the pressure transducer has substantially converged to a certain value. Subsequently, a successive pumping test can be carried out. Optionally, the successive pumping test is carried out at the same probe penetration depth, while the liquid injection flow rate Q is increased relative to the previous pumping test to a certain substantially constant value. For instance, the one or more pumping tests can comprise two pumping tests wherein the first pumping test has a constant liquid injection flow rate Q of 1 liter/minute, and the second (successive) pumping test a constant liquid injection flow rate Q of 2 liter/minute. The time for obtaining convergence of the measured response by the pressure transducer of the probe depends on varying parameters such as the liquid injection flow rate Q, depth of the probe, hydrostatic pressure state, soil parameters, etcetera. Optionally, a pumping test is maintained after convergence for a certain amount of time before going to the next successive pumping test. Alternatively, it is possible to move on to the (next) successive pumping test before convergence is reached. Instead of using measured values, it is possible to fit the measured values on a model.

Optionally, the liquid injection flow rate Q for a successive pumping test is stepwise adjusted in a steptest. Optionally, the liquid injection flow rate Q for a successive pumping test of the one or more pumping tests is stepwise increased, wherein a successive pumping test has an increased liquid injection flow rate Q, compared to the flow rate Q of a previous pumping test. Different configurations for consecutive pumping tests are possible. For example, the one or more pumping tests can comprise three consecutive pumping tests, configured to inject liquid through the liquid injection port of the probe at different liquid injection flow rates Q. A first pumping test can e.g. have a flow rate of 1 liter/minute, the second pumping test a flow rate of 3 liter/minute and a third pumping test a flow rate of 4 liter/minute.

Optionally, the one or more pumping tests include a plurality of one or more pumping tests, each one or more pumping tests of the plurality of one or more pumping tests being carried out at a different depth of penetration of the probe. In this way, the method can be used to obtain insight in detailed layering of a soil or a hydrogeological aquifer. The method consists of a combination of HPT and MPT. Different depth increments are possible. Optionally, various series of one or more pumping tests are conducted for different depths of penetration at a location where the probe is pushed into the soil. However, in a measurement campaign, such measurements can be repeated for different penetration locations of the probe. The data can be used to obtain a detailed overview of soil parameters for a measured area, including different layers for the area. In an exemplary embodiment, the data can be used to obtain a 3D or a quasi-3D graphical representation of the soil and/or aquifer, indicating determined parameters such as permeability, storativity, conductivity, etc. The depth increments for the depth of penetration of the probe wherein a series of one or more pumping tests can be carried out, can depend on the soil type or aquifer characteristics. Advantageously, the depth or plurality of depths at which the probe is configured to conduct the measurements, is carefully selected. This may be done automatically, manually or as a combination of both. For instance, software may be provided which can select measurement parameters, such as depths of penetration, depending on available data. The available data can come from previous measurement campaigns, known conditions, comparison with other data, etcetera. Optionally, measurement parameters, such as depths of penetration, can be manually set by an operator, potentially based on available data and/or experience.

Optionally, the method is carried out during a cone penetration test in which the probe is pushed into the soil at a controlled penetration rate, wherein one or more pumping tests are carried out with the probe substantially stationary with respect to the soil at a or several chosen depth(s). A cone penetration test (CPT) is a geotechnical investigation method to determine soil and groundwater characteristics. Optionally, a so-called Hydraulic Profiling Tool Cone Penetration Test, i.e. a HPT-CPT, is performed by conducting a Cone Penetration Test with a Hydraulic Profiling Tool (HPT). Permeability and storativity are important parameters in geohydrological modelling. In the past, these parameters were measured using pumping tests, grain-size correlation analyses, slugtests and/or laboratorium measurements. If none of these data are available, one had to rely on data from literature. The HPT gives a continues profile over depth. Soil parameters are measured while forcibly penetrating the HPT probe into the soil. Typically, during a HPT test, a constant cone penetration speed and a constant infiltration liquid infiltration flow is employed. Thus, the probe is pushed into the ground at a constant rate while infiltration liquid is injected into the soil through an injection port. However, the HPT test gives only a relative value of permeability, not an absolute value, and also does not give information on storativity. At certain depths of penetration, the probe can be halted to perform the one or more pumping tests. The HPT cone can be equipped with one or more porewater pressure sensors at a distance from the HPT injection point. When multiple porewater pressure sensors are present, they can be positioned at different longitudinal distances from the injection point. During HPT measurement, the HPT cone movement is stopped at a chosen depth and the injection flow rate is switched off. After dissipation of HPT-generated porewater pressure the HPT system injects infiltration liquid through the injection port in the soil at a chosen constant flow rate Q. This can be done with three different flow rates to be able to do a quality assessment of the measurements afterwards. It is also possible to repeat the same test a number of times, and/or to perform steptest with stepwise increasing or decreasing flow rates. The flowrate can be determined on the basis of the local geohydrological conditions. This results in a porewater overpressure at the pressure sensor(s). An inverse modelling can done based on the measured porewater overpressure. The inverse modelling can be done using optional equation 410.03 from Analytical Solutions of Geohydrological Problems (G. A. Bruggeman, 1999) or the like, or using publicly/commercially available geohydrogeological numerical modelling.

Optionally, one or more pumping tests during a HPT-CPT are performed at a fixed predetermined/chosen depth of penetration of the probe, preferably once a hydrostatic pressure state is obtained, for instance after a dissipation test. A continuous permeability profile of the soil can be obtained by combining HPT-CPTs with pumping tests, which may serve as a basis for a 3D soil model. For environmental data collection, a CPT cone can be basically used as an adapter to the screening sensors which provides subsurface stratigraphy through tip resistance and sleeve friction logs or other geological or environmental screening tools. By interpreting tip resistance and friction ratio, CPT data give detailed information of the subsurface lithology.

Optionally, the HPT-CPT is resumed at a controlled penetration rate after carrying out one or more pumping tests. In this way, at a certain depth of penetration one or more pumping tests can be carried out. After the one or more pumping tests, the cone penetration test can be resumed, wherein the probe is pushed at a constant rate further into the soil while injecting water through the probe. The transition between the cone penetration test and the one or more pumping tests can be accommodated by dissipation tests. For instance, before starting a first series of one or more pumping tests, at a certain depth of penetration of the probe, a dissipation test may be conducted in order to obtain a substantially hydrostatic pressure state. It is also possible that a series of one or more pumping tests are ended by a dissipation state, for obtaining a substantially hydrostatic pressure state before continuation with the cone penetration test or another series of one or more pumping tests. Different series of one or more pumping tests can be conducted for different depths of penetration of the probe into the soil. In an exemplary embodiment, after one or more pumping tests, a HPT-CPT is resumed at the same CPT probe speed and with the initial liquid injection rate. Optionally, the method further comprises processing measured data from one or more pumping tests and fitting the measured data on a computational model in order to determine the permeability and storativity at the measurement point and depth. In this way, the subsurface can be investigated by acquisition of several parameters with just one push. Permeability and storativity are important parameters in geohydrological modelling. An absolute permeability is acquired through the in-situ pumping tests. Although a HPT system can give a continuous profile over depth, the system typically provides only a relative value of permeability, not an absolute value. The continuous profile of the HPT system typically fails to provide information on storativity of an aquifer. Optionally, the acquisition of the parameters can be performed in real-time. Besides the permeability and storativity, other physical parameters of the soil and/or aquifers can also be relevant and be acquired during a measurement campaign, such as e.g. porosity, hydraulic conductivity, interporosity flow coefficient, compressibility, transmissivity, specific storage, storativity, storage coefficient, specific yield, diffusivity, hydraulic resistance, leakage factor, etcetera. It will be appreciated that hydraulic conductivity is related to permeability taking into account water properties for flow through a medium. When water is used as the injection fluid the hydraulic conductivity is measured with the HTP pumping test.

Optionally, permeability and storativity are obtained by an inverse modelling of generated liquid pressures by the one or more pumping tests. Inverse models can be employed to estimate hydrogeological parameters. Predictions, coming for instance from a mathematical model or numerical model, are matched to a set of observations, by adjusting parameters that are considered unknown or uncertain. The parameters can for instance be inferred by minimizing the sum of the squared differences between a system state calculated by a mathematical model and an observed system state. Alternative approaches to the standard least squares formulation are possible. The parameters that best reproduce the observed data are believed to be the most likely ones.

Optionally, the method further comprises determining a permeability on the basis of a ratio between the injection flow rate Q and liquid injection induced pressure P during probing. Optionally, first a relative permeability profile is obtained, from which an absolute permeability is derived. A relative permeability Q/P profile can be converted to an absolute permeability profile using linear correlation with test data gathered using a method or a system according to the present invention.

The invention further relates to a system for determining soil properties comprising a probe system including at least a liquid injection port and a pressure transducer. The probe system is arranged for penetration of a soil. The system further comprises a data acquisition system arranged for sampling measurement signals from the probe system, and a controller arranged to control the system to: push the probe system into a soil; carry out one or more pumping tests, wherein during a pumping test infiltration liquid is pumped through the liquid injection port; and measured by means of one or more pressure transducer(s), for each of the one or more pumping tests, a pressure response in the soil, resulting from the injection of liquid through the liquid injection port.

Optionally, the controller is arranged to carry out a pumping test at a chosen substantially fixed depth of soil penetration of the probe system. Optionally, additionally, sensors are provided to give an indication of the depth of soil penetration of the probe system. The sensors can be connected to the controller via wire and/or wirelessly.

Optionally, the controller is arranged to carry out a pumping test at a substantially constant liquid injection flow rate Q.

Optionally, the controller is arranged to carry out a plurality of successive pumping tests at different liquid injection flow rates Q. Optionally, the successive pumping tests are each carried out at a different liquid injection flow rate Q. In another exemplary embodiment, each successive pumping test has a higher liquid injection flow rate Q.

Optionally, the system is arranged to push the probe system into a soil at a plurality of depths of penetration of the probe system.

Optionally, the probe system includes a probe having a substantially elongated tubular shape comprising a tip facing in a longitudinal penetration direction of the probe and arranged for penetrating the soil. Advantageously, the tip can be conical so as to improve penetration into the soil. The probe can include the at least one liquid injection port and at least one pressure transducer.

Optionally, the liquid injection port and the pressure transducer are arranged at a distance from each other.

Optionally, the liquid injection port and the pressure transducer are arranged at a distance from each other with respect to a longitudinal direction of the probe. Optionally the probe includes a plurality of pressure transducers at longitudinal distances along the probe.

Optionally, the liquid injection port and the at least one pressure transducer are arranged at a distance from each other with respect to a lateral direction of a probe of the probe system.

Optionally the pumping test can be combined with one or more pressure transducers in the 3D space (X, Y, Z) around the injection point. The probe system can include a first probe including the at least one liquid injection port. The probe system can include a second probe including at least one pressure transducer. Additional pressure transducers could be placed using one or more additional probes.

The penetration depth of the probe system can be defined as the penetration depth of the probe or the penetration depth of the first probe.

Optionally, the liquid injection port and the porewater pressure transducer are arranged at a distance from each other with respect to a longitudinal penetration direction of the probe. Optionally, the pressure transducer can be arranged near or at the tip of the probe.

Optionally, the system further comprises a post-processing system for obtaining a continuous permeability profile of a soil by combining measurement data from the series of one or more pumping tests with measurement data from a hydraulic profiling tool cone penetration test. The obtained continuous permeability profile of a soil may serve as a basis for a three-dimensional soil model.

Optionally, the system is arranged on a movable unit. A movable unit can for instance be a vehicle, truck, tracktruck, stand-alone device, crawler, CPT-crawler, standard CPT-truck, CPT-minicrawler, floating device, borehole device, etcetera. Depending on the terrain, area and space conditions the right choice for a movable unit can be chosen. The system can also be mountable on vehicles, boats, pontoons, etcetera. Different combinations are possible.

The invention further relates to a computer program product for determining soil properties using a probe comprising at least a liquid injection port and a porewater pressure transducer. The computer program product comprises instructions for causing a processor to perform the steps of providing a first signal for carrying out a series of one or more pumping tests wherein infiltration liquid is pumped through the liquid injection port of the probe; providing a third signal for measuring by means of the porewater pressure transducer, for each of the series of one or more pumping tests, a pressure response in the soil resulting from the injection of liquid through the liquid injection port; receiving for each of the one or more pumping tests measured data; and determining from the measured data of the series of one or more pumping tests information representative of soil properties. Optionally, the computer program product may be configured to initiate one or more pumping tests conducted at different substantially constant liquid injection flow rates Q. Also, a plurality of series of one or more pumping tests are possible. The computer program product may further be configured to give instructions to obtain a substantially hydrostatic pressure state during a measurement, for example by initiating a dissipation test. In this way, it is possible to start the one or more pumping tests from a substantially hydrostatic pressure state by performing a dissipation test prior to starting a one or more pumping tests. A pressure transducer for measuring the generated liquid/water pressures can be utilized to determine a pore water pressure, which values can be obtained by the computer program product. Further, the computer program product can be arranged to determine measurement depths of soil penetration of the probe where one or more pumping tests need to be conducted, and provide instructions so as to perform one or more pumping tests at the different depths of penetration. Additionally or alternatively, the computer program product can be configured to control a measurement campaign comprising a plurality of series of one or more pumping tests according to the present invention, for instance carried out at different depths of soil penetration by the probe and/or at different locations of soil penetration at the surface of the soil. Further, in an exemplary embodiment, the computer program product can be configured to evaluate the obtained information representative of soil properties by performing an analysis of said information, optionally followed by a presentation of an analysis to a user, e.g. either automatically or on command by a user.

Further, the system according to the current invention may comprise a non-transitory computer-readable medium, which has program instructions stored thereon that are executable by at least one processor to provide the functionality described by the method herein.

It will be appreciated that any of the aspects, features and options described in view of the method apply equally to the described system and computer program product. It will also be clear that any one or more of the above aspects, features and options can be combined.

BRIEF DESCRIPTION OF THE DRAWING

The invention will further be elucidated on the basis of exemplary embodiments which are represented in a drawing. The exemplary embodiments are given by way of non-limitative illustration. It is noted that the figures are only schematic representations of embodiments of the invention that are given by way of non-limiting example.

In the drawing:

FIG. 3a shows a schematic side view of a probe according to a preferred embodiment of the present invention;

FIG. 3b shows a schematic side view of a probe;

DETAILED DESCRIPTION

Figure 1B:
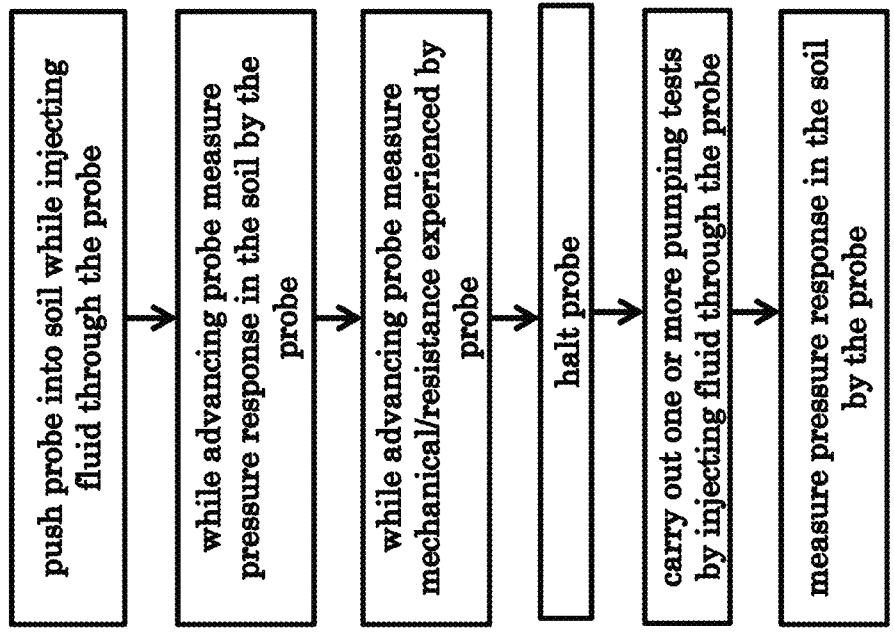
FIG. 1B shows a flow chart of an embodiment of a method according to a preferred embodiment of the present invention.
Figure 1A:
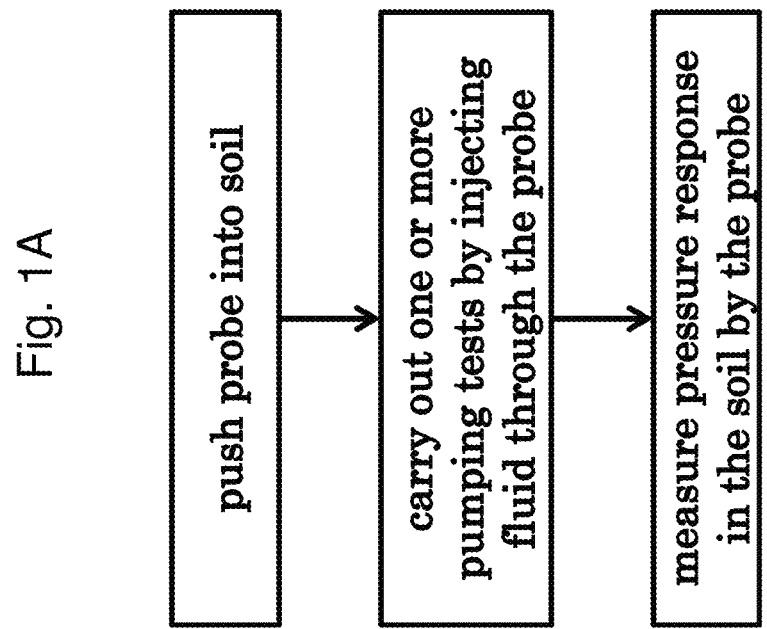
FIG. 1A shows a flow chart of an embodiment of a method according to a preferred embodiment of the present invention.

FIG. 1A shows a flow chart of a method according to the invention. The method can be used for determining soil properties by use of a probe comprising at least a liquid injection port and a pressure transducer. The probe is pushed into a soil for carrying out one or more pumping tests at predetermined depths. During a pumping test an infiltration liquid is pumped though the liquid injection port of the probe. In this example the infiltration liquid is water. The pressure response resulting from the injection of water through the liquid injection port in the soil is measured by means of the pressure transducer arranged on the probe. The pressure response can be measured for each of the one or more pumping tests. The soil testing system can be used for measuring soil parameters while the probe is penetrated into the soil.

FIG. 1B shows a flow chart of a method according to the invention wherein the pumping test is combined with a hydraulic profiling tool, HPT, and/or cone penetrometer, CPT, test. The probe is pushed into a soil while an infiltration liquid is pumped though the liquid injection port of the probe. During advancement of the probe through the soil the pressure response of the soil/groundwater system against liquid injection can be determined. Also during advancement, mechanical resistance and/or friction experienced by the probe can be determined. The probe is halted at a predetermined depth. One or more pumping tests are performed while the probe is halted at the predetermined depth. During a pumping test an infiltration liquid is pumped though the liquid injection port of the probe. The pressure response resulting from the injection of liquid through the liquid injection port in the soil is measured by means of the pressure transducer arranged on the probe. The pressure response can be measured for each of the one or more pumping tests.

Figure 2:
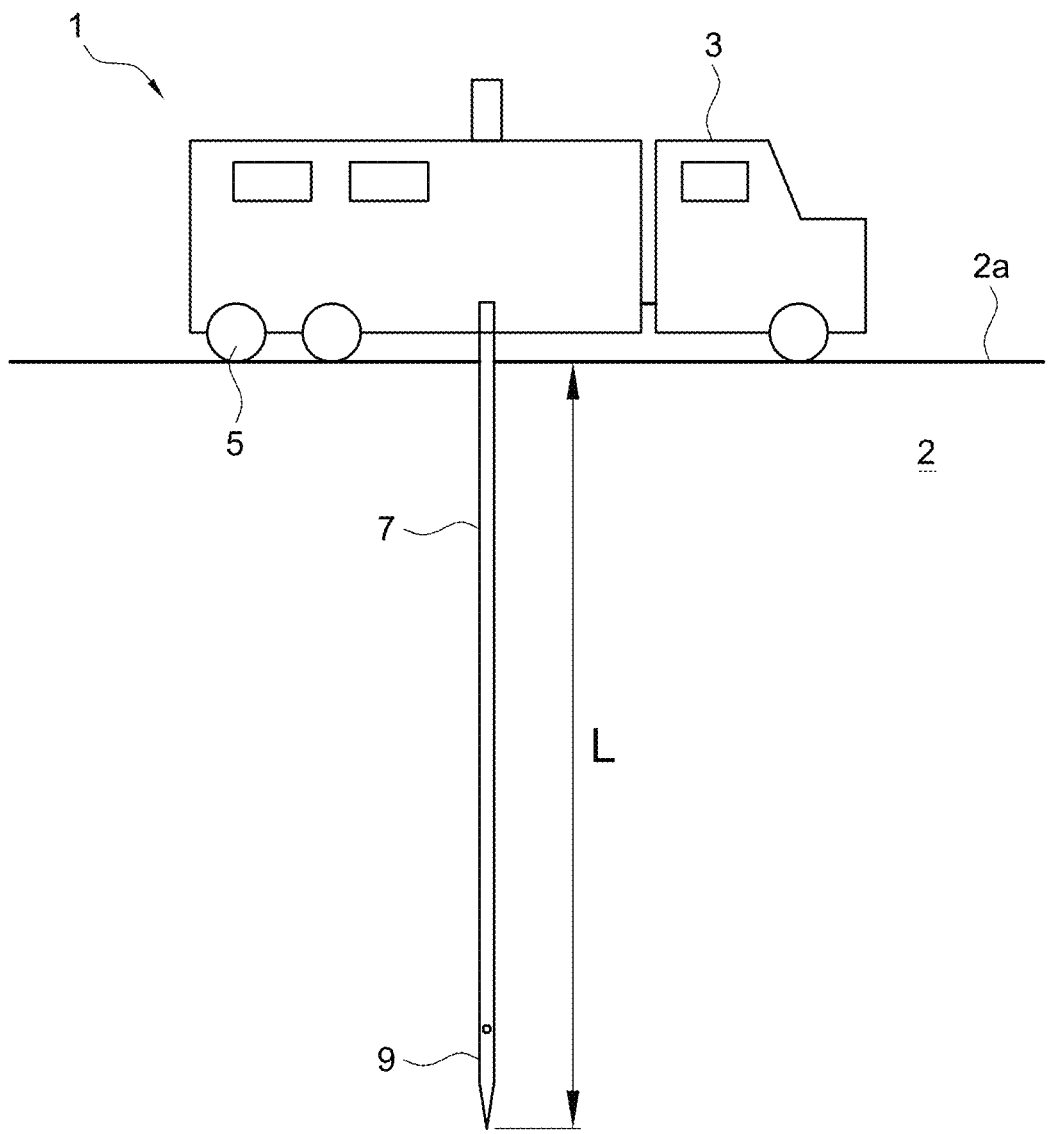
FIG. 2 shows a schematic side view of an embodiment of a system according to a preferred embodiment of the present invention.

FIG. 2 shows a schematic side view of an embodiment of a system 1, which can be employed during soil penetration tests for subsurface characterization of a soil 2. The system 1 comprises a probe 9 comprising at least a liquid injection port and a pressure transducer. The probe 9 is arranged for penetration of the soil 2. The system further comprises a data acquisition system arranged for sampling measurement signals from the probe, a controller arranged to control the system to push the probe 9 into the soil 2 and carry out one or more pumping tests, and measure by means of a pressure transducer, for each of the one or more pumping tests, a pressure response in the soil, resulting from the injection of liquid through the liquid injection port. The system 1 can comprise a truck 3. The truck 3 according to this embodiment has wheels. However, tracks or a combination of wheels and tracks can also be arranged. Other arrangements are also possible, e.g. the system 1 may be movable by another transportation unit. The truck 3 may further comprise a plurality of stabilizers to provide support and to improve stability during the penetration tests. The system 1 can further comprise a rod 7 which is coupled to the probe 9, and means for forcibly penetrating the probe 9 into the soil 2 by pushing the rod 7, wherein a depth of penetration L and a penetration rate of the probe 9 can be controlled by the controller. The rod 7 is used to push the probe 9 into the soil, and can include a plurality of sub-elements, such as a plurality of rod sections connected to each other. Other solutions are possible for pushing the probe 9 into the soil. The pushing force for penetration of the probe into the soil 2 can be supplied by a hydraulic pushing arrangement, arranged in the truck 3. The weight of the truck 3 can provide the reaction force for pushing against the rod 7 which is connected to the probe 9 which is forcibly penetrated into the soil 2. Other solutions for providing the reaction force are possible. Further, the system comprises a pump arranged to provide liquid, such as water, to the probe, so as to enable the injection of liquid into the soil through the liquid injection port arranged on the probe.

The system 1 further comprises a digital computer which can be coupled to the probe 9 and its sensors to receive measurement data from the sensors. The data acquisition system can be arranged to receive electrical signals from the sensors of the probe 9. Also, the digital computer can be coupled to the data acquisition system so as to receive the acquired electrical signals or signals representative for the acquired electrical signals. The digital computer can be arranged for processing the electrical signals to provide an analysis of the measurement results so as to determine and/or calculate soil parameters and characteristics.

Further, the system can comprise an interface, such as a monitor, coupled to the digital computer for displaying a soil analysis which can include the determined soil parameters, such as e.g. permeability and storativity. The analysis may be performed for different depths of penetration L. The results from a measurement campaign may be combined to provide a general overview of the soil parameters over an area or volume.

The digital computer can be arranged in a measurement unit in the truck 3 or at a remote unit. The measured data may be received by a digital computer through a wired connection or wireless connection. In case of wireless data communication, a wireless connection device may be arranged to transfer signals through mobile data transfer protocols such as 3G, 4G, 5G, etc. However, other wireless protocols such as WiFi (e.g., a wireless communication conforming to the IEEE 802.11 standard or other transmission protocol) or LoRa may also be employed to obtain a wireless communication. A combination of wireless protocols is possible.

The system 1 may be implemented in or may take the form of a vehicle. Alternatively, the system may be implemented in or take the form of other vehicles, such as cars, recreational vehicles, trucks, agricultural vehicles, construction vehicles and robotic vehicles. It also perceivable that a plurality of systems 1 are included in a vehicle.

FIGS. 3a and 3b show embodiments of the probe 9 comprising a liquid injection port 11 and a pressure transducer 13. FIG. 3a shows a schematic side view of the probe 9 having a substantially elongated tubular shape comprising a tip 17 facing in a longitudinal penetration direction 19 of the probe 9 and arranged for penetrating the soil 2. In this embodiment, the tip 17 of the tubular probe 9 has a conical shape, however, other shapes are possible. The liquid injection port 11 and the pressure transducer 13 of the probe 9 are arranged at a distance D from each other with respect to a longitudinal penetration direction of the probe 9. FIG. 3b shows a schematic side view of the probe 9 coupled with rod 7 for being pushed into the soil 2. At a certain depth of penetration L into the soil 2, the one or more pumping tests can be conducted, during which the infiltration liquid is pumped through the liquid injection port 11 of the probe 9 in the liquid infiltration flow direction 15 out of the probe 9. By means of the pressure transducer 13, for the one or more pumping tests, a pressure response in the soil 2 resulting from the injection of a liquid through the liquid injection port 11 can be measured. The one or more pumping tests can be carried out at a predefined/chosen substantially fixed depth of soil penetration L of the probe 9. Liquid, such as water, can be injected into the soil 2 through the water injection port 11 at a certain water injection flow rate Q which can be adjusted and controlled. The one or more pumping tests can be carried out at a substantially constant water injection flow rate Q, while in case of a plurality of pumping tests, successive pumping tests at a certain depth of penetration L can be carried out at different water injection flow rates Q.

A hydraulic profiling tool, HPT, probe 9 can be used to carry out a cone penetration test, CPT in a hydraulic profiling tool cone penetration test, HPT-CPT. Herein the HPT probe 9 is pushed into the ground or soil 2 at a constant rate while water is injected at a constant flow rate into the soil through a water injection port 11 arranged on the HPT probe 9. A HPT-CPT measurement can be used to evaluate hydraulic properties of a site sub-surface. The system 1 can comprise a HPT probe 9 comprising a tip or cone equipped with one or more water pressure sensors at a distance D from a HPT probe 9 water injection port 11, i.e. injection point. During a HPT measurement the HPT probe is advanced through the soil while injecting water via the injection port 11 at a constant flow rate. During advancement a pressure response of the soil/groundwater system against water injection is determined. During a CPT measurement the probe is advanced through the soil. During advancement mechanical tip resistance, and optionally sleeve resistance, may be measured. A HPT-CPT measurement combines the HPT and the CPT measurement. During a HPT measurement, the HPT probe movement can be stopped at a certain depth of penetration L. After dissipation of water pressures generated as a result of the HPT measurement, the system 1 can carry out one or more pumping tests wherein water is injected in the soil 2 through the injection port 11. For instance, four pumping tests can be carried out, wherein four different water injection flow rates Q are used for the different pumping tests. The different water injection flow rates can be used to perform a quality assessment of the measurements afterwards by analyzing the pressure response measured by the pressure transducer 13 of the HPT probe 9. The water injection flow rate through the water injection port 11 of the HPT probe 9 can induce water overpressures, which may depend on the local geohydrological conditions, and which can be sensed/measured by the pressure transducer 13. After finishing a field measurement inverse modelling can be performed on the measured water overpressure. The inverse modelling can be performed using analytical solutions or using geohydrogeological numerical modelling. The HPT-CPT measurement may be continued after performing one or more pumping tests at a certain depth. The probe 9 may e.g. be pushed further into the soil 2. The HPT probe 9 may pushed into the soil 2 at the same constant rate while water is injected at the constant flow rate as before the pumping tests. It will be appreciated that the HPT-CPT measurement may be resumed after pore water pressure of the preceding pumping tests has dissipated. It is possible that after the HPT-CPT measurement is resumed after water injection has been restored to the level of the initial HPT-CPT measurement, and water pressure has come to an equilibrium.

Figure 3C:
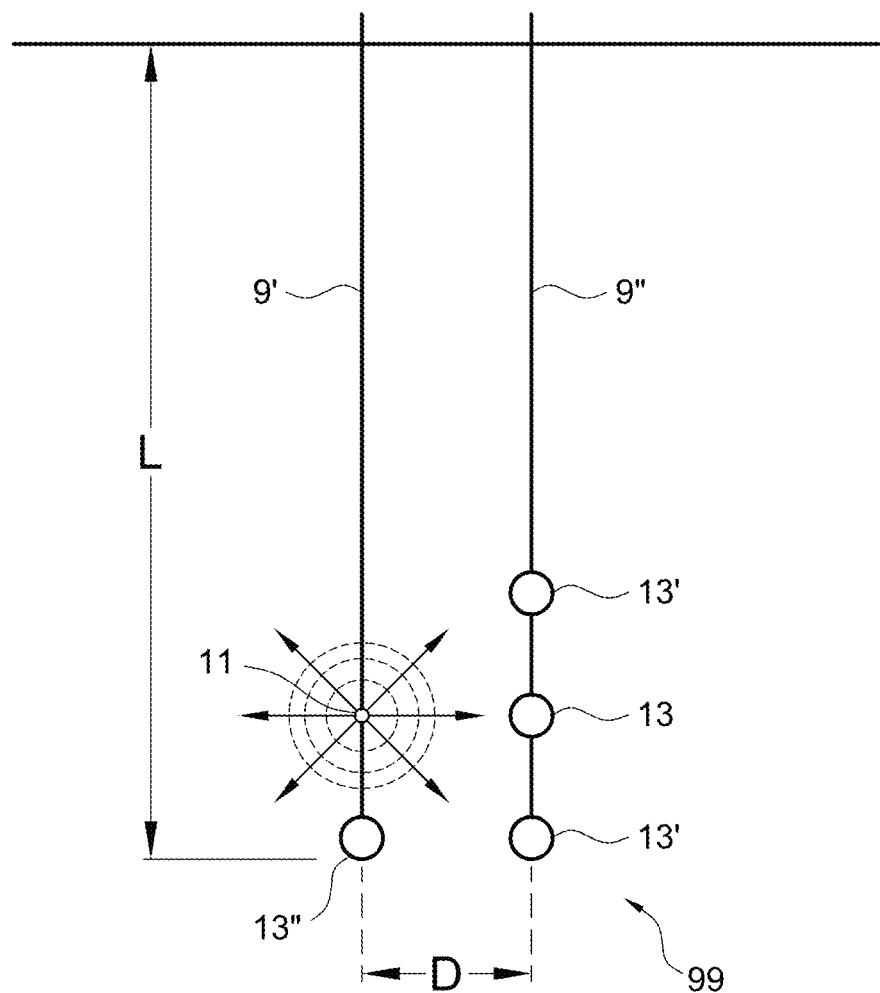
FIG. 3c shows a schematic side view of a probe.

FIG. 3c shows an embodiment of a probe system 99 comprising a first probe 9' and a second probe 9". 'The first and second probes 9', 9" are laterally spaced from each other. The first probe 9' comprises the liquid injection port 11. The second probe 9" comprises the pressure transducer 13. In this example, the probe system 99 comprises further pressure transducers 13', 13". The liquid injection port 11 and the pressure transducer 13 of the probe system 99 are arranged at a distance D from each other with respect to a lateral direction of the probe 9'. The one or more pressure transducers in the 3D space around the injection point can be used to derive horizontal and/or vertical permeability and storativity from the measured pressure response on the injected liquid Q. For example, the pressure transducer 13 can be used to determine the horizontal permeability and storativity. The pressure transducer 13" can be used to determine the vertical permeability and storativity. Optionally the horizontal and/or vertical permeability and storativity can be derived using numerical or analytical calculations with an inverse modelling technique.

Figure 4:
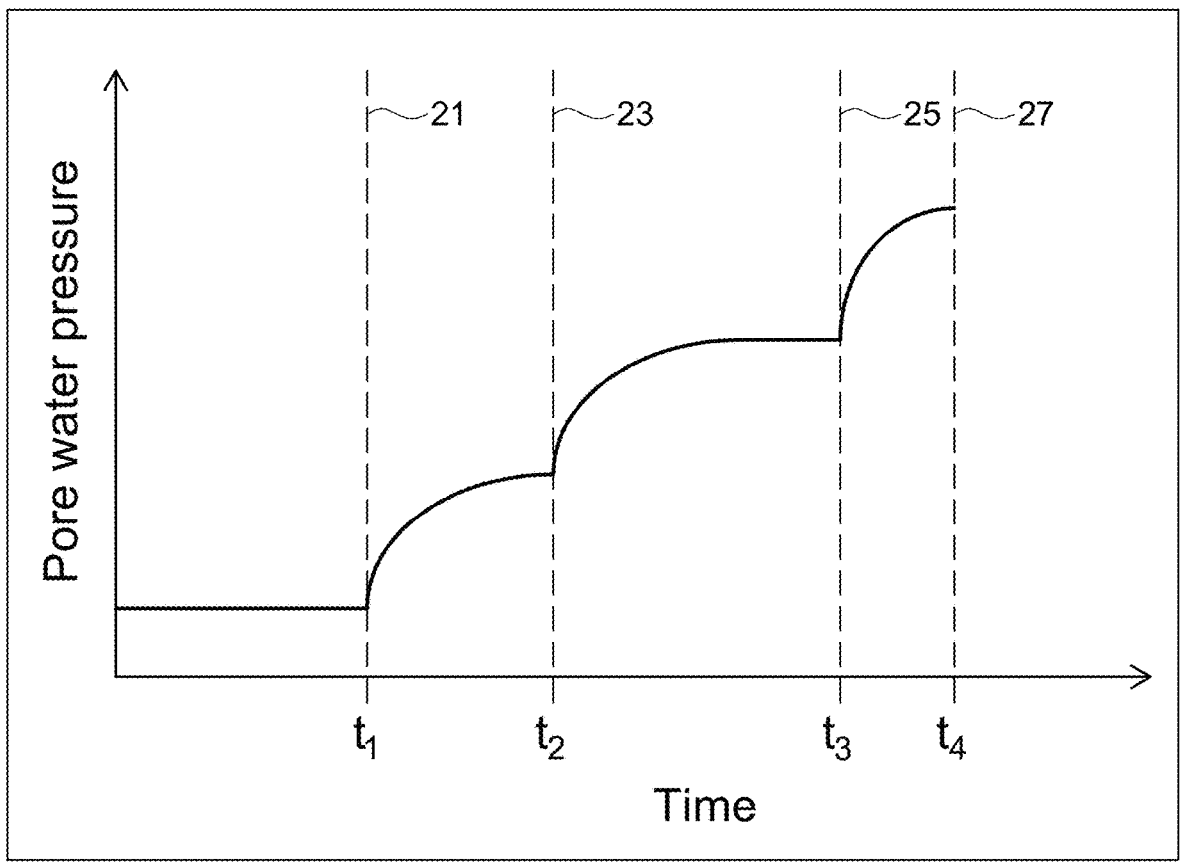
FIG. 4 shows a graph, illustrating pore water pressure characteristics during pumping tests.

FIG. 4 shows a graph, illustrating pore water pressure characteristics during pumping tests. The probe 9 including a liquid injection port 11 and a pressure transducer 13 is pushed into a soil 2 at a certain depth of penetration L, where, in this example, three consecutive pumping tests are carried out without waiting time between the three pumping tests. This is also referred to as steptest. Similar pumping tests can be carried out at different penetration locations and/or depths of penetration L. During a pumping test infiltration liquid, such as water, is pumped through the liquid injection port 11 of the probe 9 into the soil 2. By means of the pressure transducer 13 a pressure response in the soil 2 resulting from the injection of water through the liquid injection port 11 is measured for three different injection flow rate pumping test. In FIG. 4, the pore water pressure is plotted in function of time for the successive pumping tests. In this example, prior to starting the pumping tests, water injection through the liquid injection port 11 is stopped. At time t1, indicated by line 21, the first pumping test with injection rate Q1 of the three pumping tests is initiated. At this point of time, water is injected and pumped through the injection port 11 of the probe 9 at a first liquid injection flow rate Q1. The liquid injection flow rate Q is kept constant and the pore water pressure has substantially converged to a steady state value at time t2. At this time, t2, the first pumping test is finalized and the second pumping test is started, indicated by line 23. During the second pumping test, water is injected and pumped through the injection port 11 of the probe 9 at a second liquid injection flow rate Q2, different from the first injection flow rate of the first pumping test Q1. In this example, the second liquid injection flow rate Q2 is higher than the first liquid injection flow rate Q1, which causes the pore water pressure to substantially converge to a second value higher than the first converged value of the pore water pressure in the first pumping test. When the pore water pressure in the second pumping test has substantially converged, a third pumping test is initiated at time t3, indicated by line 25, wherein again the liquid injection flow rate is increased with respect to the previous pumping test, i.e. the second pumping test. The pore water pressure during the third pumping test converges again to a certain value. The third pumping test is finalized at time t4, indicated by line 27. Although, a steptest including three pumping tests are illustrated in this example, it is also possible to carry out a steptest including another number of pumping tests, for example one pumping test. Other quantities such as two, four, five, ten, twelve, twenty, etc. pumping tests can be carried out. It is also possible that a single pumping test is performed at the penetration location. It is also possible that a plurality of pumping tests is carried out with waiting times in between the pumping tests at the penetration location. During the waiting time liquid injection may be halted or the liquid injection rate set at a reference level. The three pumping tests in this example can also be considered as a series of one or more pumping tests, wherein such series of pumping tests can be carried out at different penetration locations and/or depths of penetration L. The series of pumping tests can be different with respect to each other, e.g. may comprise a different number of pumping tests, different liquid injection flow rates Q, etcetera.

Figure 5:
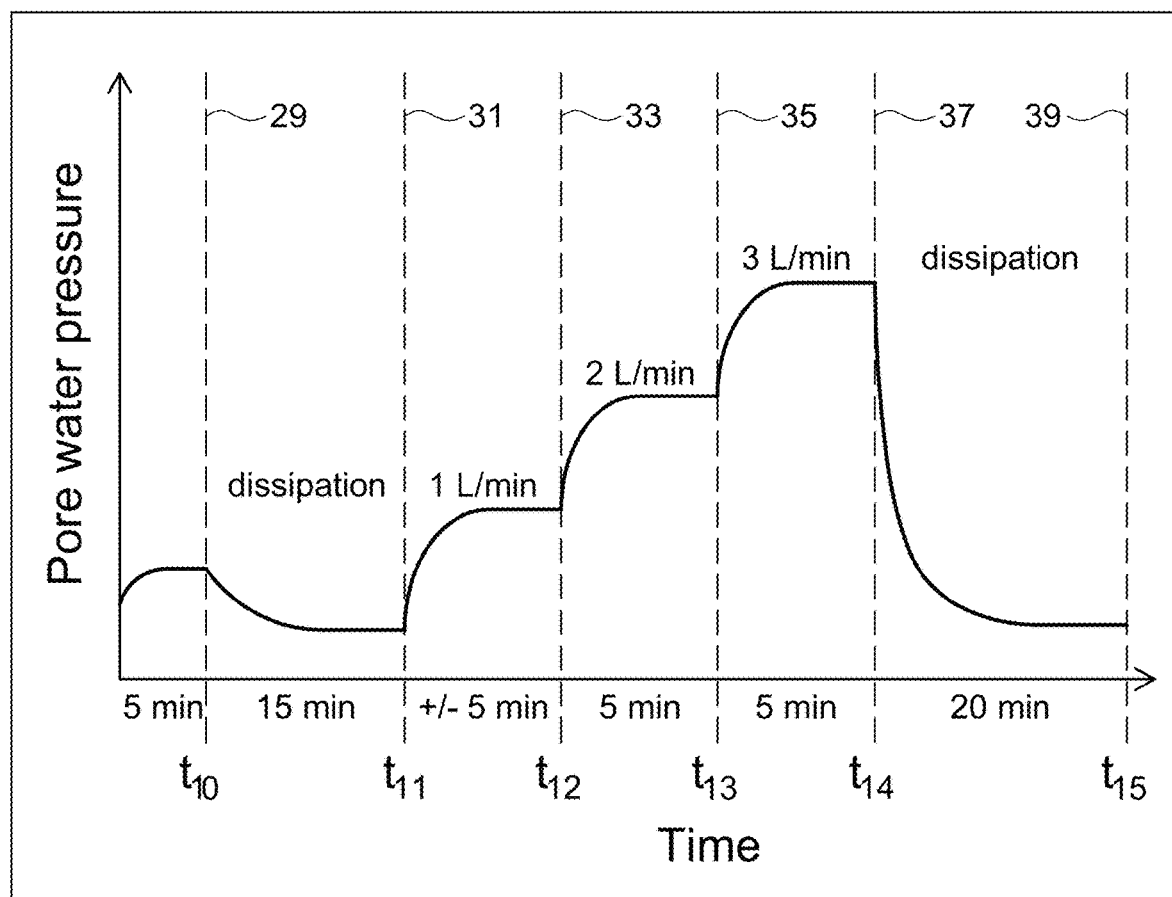
FIG. 5 shows a graph, illustrating pore water pressure characteristics.

FIG. 5 shows a graph, illustrating pore water pressure characteristics during pumping tests. The probe 9 including a liquid injection port 11 and a pressure transducer 13 is pushed into a soil 2 at a certain depth of penetration L, where, in this example, three pumping tests are carried out. During a pumping test infiltration liquid, such as water, is pumped through the liquid injection port 11 of the probe 9 into the soil 2. By means of the pressure transducer 13 a pressure response in the soil 2 resulting from the injection of water through the liquid injection port 11 is measured for each of the three pumping tests. In this example, the pore water pressure is plotted in function of time for successive pumping tests and dissipation tests. Prior to starting the three pumping tests, a dissipation test is carried out, wherein pumping of infiltration liquid (water) through the liquid injection port 11 of the probe 9 with Q0 is stopped after the stopping the HPT at a certain depth in order to obtain a substantially hydrostatic pressure state. At time t10, indicated by line 29 a dissipation test is initiated. After a time a substantially hydrostatic pressure state is obtained, after which, at time t11, indicated by line 31, the first pumping test of the three pumping tests can be initiated. At this point of time, water is injected and pumped through the liquid injection port 11 of the probe 9 at a first liquid injection flow rate Q1, for example at 1 liter/minute. The liquid injection flow rate Q1 is kept constant and as a result the pore water pressure has substantially converged to a certain steady state value at time t12. At this time, t12, indicated by line 33, the first pumping test is finished and the second pumping test is started. During the second pumping test, water is injected and pumped through the injection port 11 of the probe 9 at a second liquid injection flow rate Q2, different from the first injection flow rate Q1 during the first pumping test, for example 2 liter/minute. The second injection liquid injection flow rate Q2 is higher than the first liquid injection flow rate Q1, which causes the pore water pressure to substantially converge to a second steady state value wherein the converged value is higher than the converged value of the pore water pressure as a result of the first pumping test. After convergence of the pore water pressure in the second pumping test, a third pumping test is initiated at time t13, indicated by line 35, wherein again the liquid injection flow rate is increased with respect to the previous pumping test, i.e. the second pumping test, for example from 2 liter/minute to 3 liter/minute. The pore water pressure during the third pumping test converges again to a certain value. The third pumping test is finalized at time t14, indicated by line 37. In this example, the third pumping test is followed by another dissipation test, at time 14, wherein pumping of infiltration liquid through the liquid injection port 11 of the probe 9 is stopped in order to obtain a substantially hydrostatic pressure state. This dissipation test is finalized at time t15. In this example, the individual pumping tests take approximately 5 minutes. However, other durations are possible and can be dependent on the hydrogeological properties of the soil. Although three pumping tests are illustrated in this example, another number of pumping tests can be carried out. Also, multiple series of one or more pumping tests can be carried out by the system 1. The series of one or more pumping tests can be different with respect to each other, e.g. may comprise a different number of pumping tests, different liquid injection flow rates Q, etcetera. After finishing the pumping tests, the probe may be advanced to a next penetration depth. During advancement a HPT or HPT-CPT measurement may be carried out.

Figure 6B:
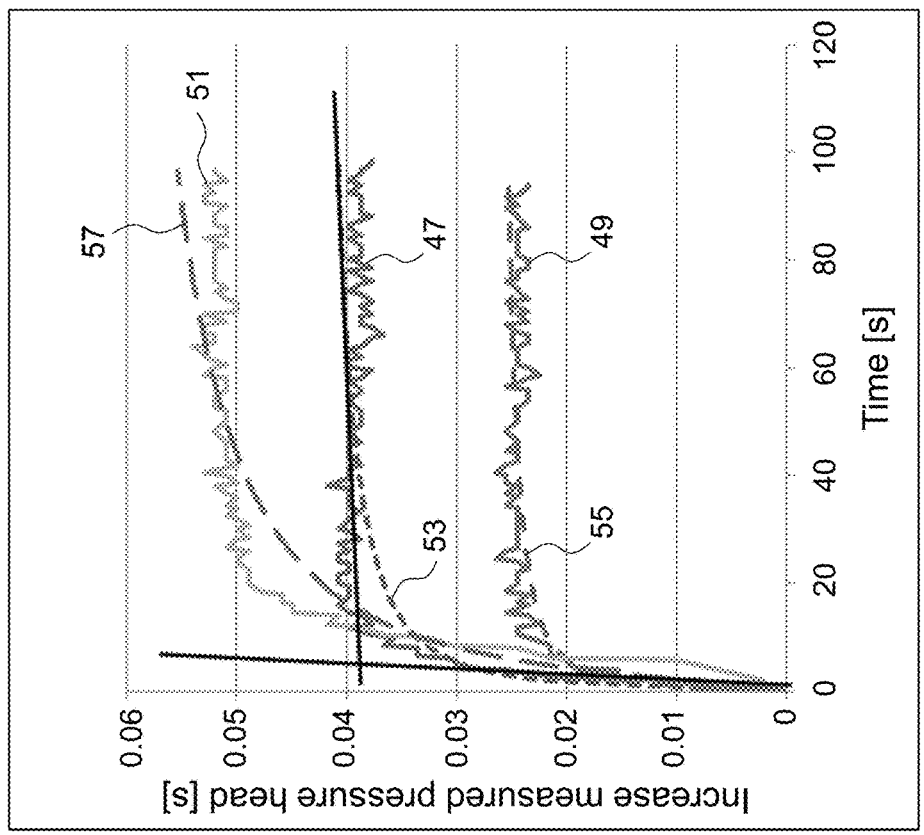
FIG. 6b shows a graph, illustrating increase in measured pressure head.
Figure 6A:
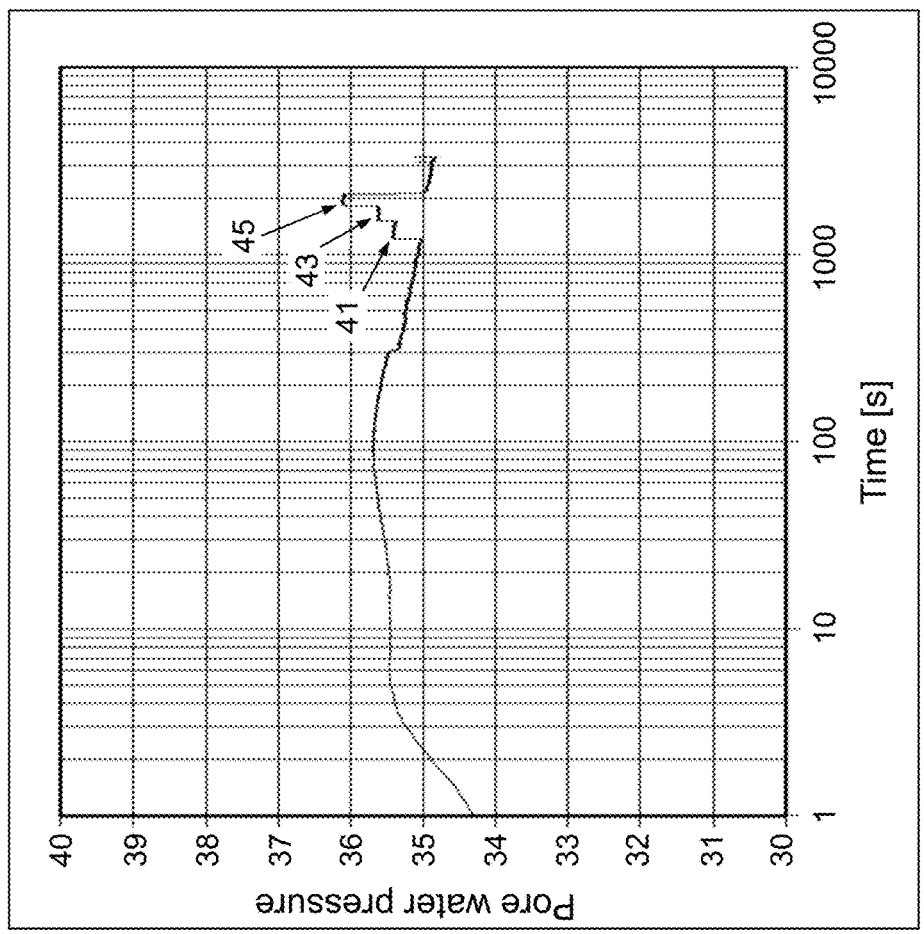
FIG. 6a shows a graph, illustrating pore water pressure characteristics.

FIG. 6a illustrates a graph, illustrating pore water pressure characteristics. The measured pore water pressure (no correction) is plotted in function of a logarithmic time scale. In this example, the pore water pressure during three pumping tests 41, 43, 45 is shown in function of time. Prior to the first pumping test 41, a dissipation test is carried out to obtain a substantially hydrostatic state. During the successive pumping tests, the water injection flow rate Q is increased step wise, resulting in a step wise increase at the pore water pressure. After the third pumping test 45, a dissipation test is carried out, resulting in a drop in the measured pore water pressure.

FIG. 6b shows a graph, illustrating the increase in measured pressure head as a result of the pumping tests according to the example shown in FIG. 6a. For the first pumping test 41, the increase in measured pressure head 47 can be fitted on a model calculated curve 53. Further, for the second and third pumping test 43 and 45, the increase in measured pressure head 49 and 51 can be fitted on model calculated curves 55 and 57, respectively. The model curves 53, 55, 57 can for instance be used to determine steady state convergence values and for deriving soil properties, such as permeability and storativity.

The increase in pore water pressure caused by injecting liquid into the soil can be a measure for the permeability of the encountered soil layers. The ratio between the injection flow rate and pressure Q/P can give the hydraulic index or relative permeability.

The measured pore water pressure is the sum of the hydrostatic pore water pressure, the pore water pressure buildup due to injection and air pressure. The hydrostatic pressure can be determined by dissipation tests.

The parameters hydraulic conductivity K and storage coefficient Ss can be determined for each pumping test by fitting a model on the measured pore water pressure increase, e.g. by the use of a model with a transient groundwater flow equation.

The relationship between Q/P and K can be described by $K=[1/C] \cdot Q/P$, wherein $[1/C]$ is constant. This equation describes a positive linear relationship between Q/P and K and approaches the origin if K approaches 0. The constant 1/C can be determined by using the determined permeability values and corresponding Q/P values from the one or more pumping tests. The relationship between conductivity K and Q/P can be plotted in a graph. A trend line going through the origin is then plotted for the data, wherein the slope of the trend line can indicate the constant 1/C.

The determined K value gives a measure of the permeability and storativity of the layer between the infiltration point, i.e. liquid injection port, and conus tip. The increase in pressure at a given injection flow rate depends on the permeability of the soil and the distance of the point of measurement to the injection point/port. The rate at which the pressure increase becomes constant after a change in flow rate (i.e. the duration of the transient phase/lag time) gives an indication of the storativity and hence the rate of reaction of the soil on variations in pressure. Permeability is important for groundwater flow calculations, wherein groundwater flow rate plays a role. Storativity is important to carry out time-dependent groundwater flow calculations. By use of the one or more pumping tests, a relative permeability Q/P can be transformed to an absolute permeability.

Figure 7:
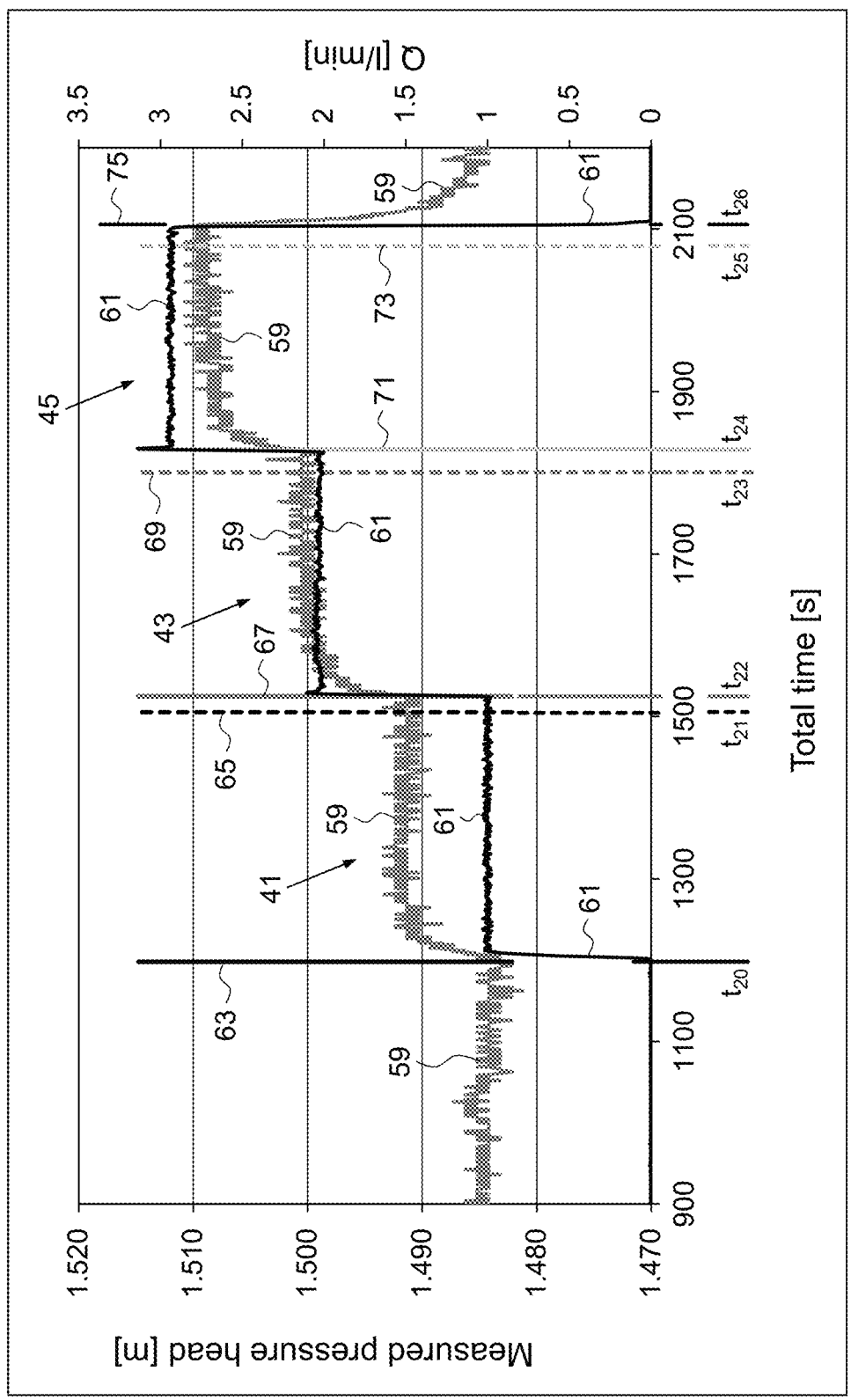
FIG. 7 shows a graph, illustrating measured pressure head and corresponding injection flow rate.

FIG. 7 shows a graph, illustrating measured pressure head (first x-axis) and liquid injection flow rate Q (second x-axis) as a function of time. Curve 59 indicates the pressure head and curve 61 indicates the liquid injection flow rate Q through the liquid injection port 11 in the probe 9. In this example, the liquid injection flow rate Q is initially zero prior to starting three pumping tests 41, 43 and 45. This can for instance be a result of a dissipation test, wherein pumping of infiltration liquid through the liquid injection port 11 of the probe 9 is stopped in order to obtain a substantially hydrostatic pressure state. A substantially hydrostatic pressure state prior to starting pumping tests can be advantageous. Line 63 indicates the start at time t20 of the first pumping test 41, wherein infiltration liquid is pumped through the liquid injection port 11 of the probe 9 and injected into the soil 2 at a constant liquid injection flow rate Q, of approximately 1 liter/minute in this example. During the first pumping test 41, the pressure head substantially converges to a steady state value. The measurement of the first pumping test 41 is ended at time t21, indicated by line 65. However, the liquid injection flow rate Q during the first pumping test 41 is maintained until the second pumping test 43 is started at time t22, indicated by line 67. The liquid injection flow rate Q through the liquid injection port 11 of the probe 9 is increased to approximately 2 liter/minute in this example. As a result of the increase in liquid injection flow rate Q, the measured pressure head converges to a new steady state value. The measurement of the second pumping test 43 is ended at time t23, indicated by line 69. However, the liquid injection flow rate Q during the second pumping test 43 is maintained until the third pumping test 45 is started at time t24 indicated by line 71. The liquid injection flow rate Q is again increased, to approximately 3 liter/minute in this example. As a result of the increase in liquid injection flow rate Q in the third pumping test 45, the measured pressure head converges to a new higher steady state value. The measurement of the third pumping test 45 is ended at time t25, indicated by line 73. However, the liquid injection flow rate Q during the third pumping test 45 is maintained in this example until time t26, indicated by line 75, at which liquid injection through the liquid injection port 11 of the probe 9 is stopped, causing a drop of the measured pressure head. A dissipation test can be carried out, wherein pumping of infiltration liquid through the liquid injection port 11 of the probe 9 is stopped in order to obtain a substantially hydrostatic pressure state.

Figure 8:
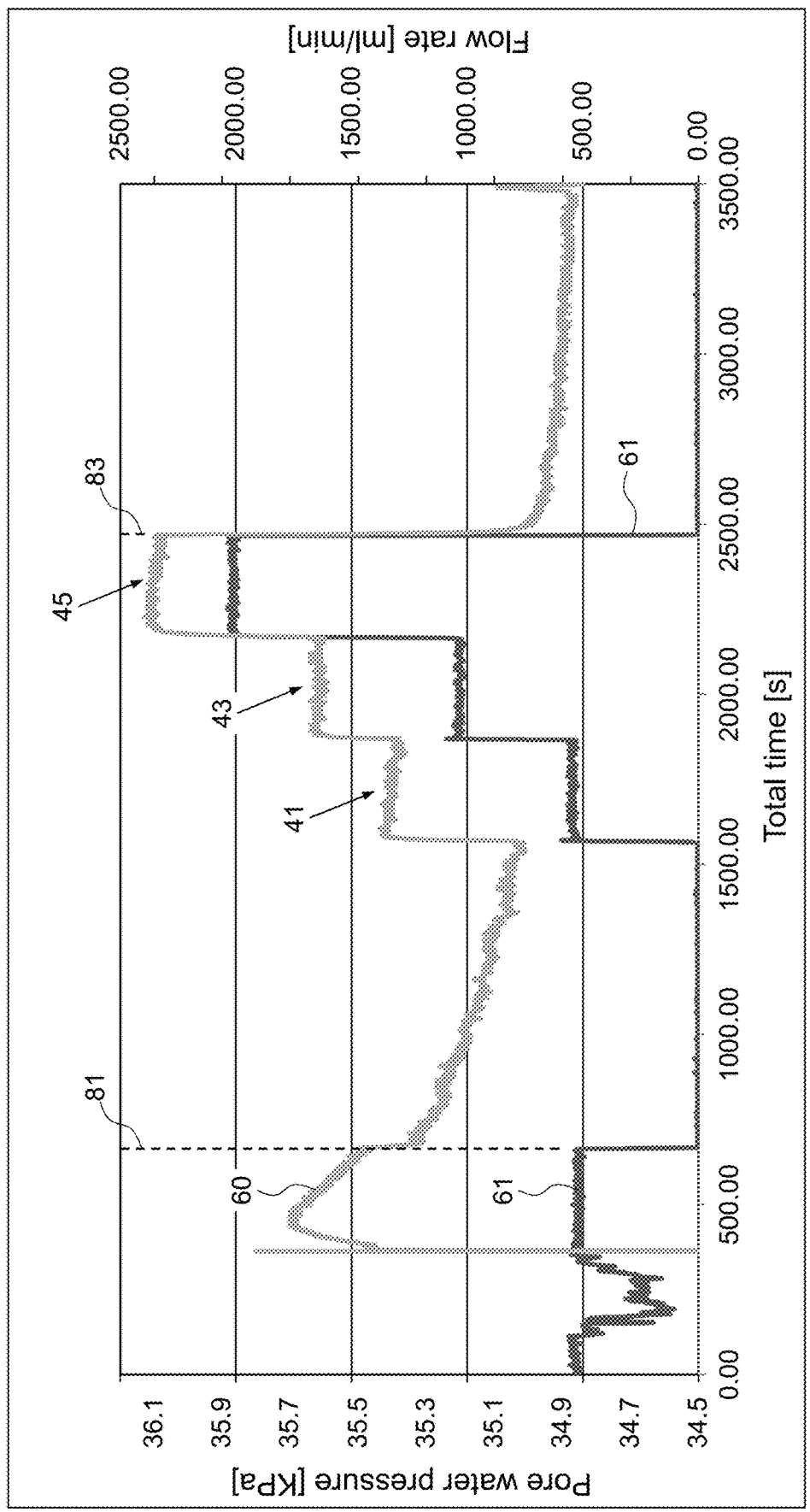
FIG. 8 shows a graph, illustrating pore water pressure and corresponding injection flow rate.

FIG. 8 shows an exemplary graph illustrating measured pore water pressure and flow rate during different pumping tests. The example show three successive pumping tests 41, 43 and 45 carried out at different water injection flow rates Q, namely 0.5 liter/minute, 1 liter/minute and 2 liter/minute, respectively. Although a steptest including three pumping tests 41, 43 and 45 is illustrated, another number of pumping tests is possible. Any combination of pumping tests, e.g. in series, with or without intermediate periods of rest, at stepped flow rates or otherwise, can be performed. For instance, in another exemplary embodiment, only one pumping test can be carried out. It is also possible that one or more pumping tests are carried out at different depths of penetration L of the probe 9 into the soil 2. Curve 60 indicates the measured pore water pressure at measurement point 13 and curve 61 indicates the liquid injection flow rate Q at the injection port 11. In this example, the liquid injection flow rate Q0 used during the HPT measurement is stopped prior at line 81 to starting the series of pumping tests 41, 43, 45. The resulting pore pressure decrease corresponds to a dissipation test, which will eventually reach a substantially hydrostatic pressure state. Another dissipation test is carried out after the last pumping test of three pumping tests has ended at line 83.

In an exemplary embodiment, a HPT probe 9 is arranged to evaluate hydraulic properties of the site subsurface. While the HPT probe 9 is advanced through the soil 2, liquid or water can be injected at a constant liquid injection flow rate Q through a water/liquid injection port 11 on a side of the HPT probe 9. An in-line pressure sensor can measure the response pressure of the soil/groundwater system against water injection by the HPT probe 9 through the water injection port 11. The water flows into the soil layers at a certain rate and with a certain pressure build up depending on the hydraulic properties of the soil 2. For instance, a low response pressure can indicate a large grain size, and the ability to easily transmit water. A high response pressure, however, can indicate a small grain size and the inability to transmit water. Pressure and water injection flow rate can both be logged versus depth. At a certain depth of penetration L, the HPT probe 9 movement can be stopped, followed by one or more pumping tests, wherein water is injected into the soil 2 at the depth of penetration L by the HPT probe 9 through the water injection port 11 of the HPT probe 9. The resulting water pressure is measured by the pressure transducer 13 of the HPT probe 9. The HPT probing can then, if necessary, be continued and pushed further to a next depth of penetration L where one or more pumping tests are going to be conducted.

In another exemplary embodiment, at a certain depth of penetration L, the HPT probe 9 movement can be stopped as well as the HPT injection, followed by a dissipation test so as to allow dissipation of HPT generated pressures in the soil 2. After the dissipation test, one or more pumping tests can be conducted at a substantially fixed depth of penetration, where water is injected into the soil 2 by the HPT probe 9 through the water injection port 11 at a substantially constant water injection flow rate Q. The water injection flow rate Q for the different pumping tests can be different. The resulting water pressure is measured by the pressure transducer 13 of the HPT probe 9. The one or more pumping tests can be followed by a dissipation test for dissipation of the generated overpressures by the one or more pumping tests. The HPT probing can then be continued to a next depth of penetration L where one or more pumping tests are going to be conducted. Inverse modelling can be employed on generated waterpressures resulting in permeability (K) and storativity (Ss). The HPT relative permeability (Q/P) profile can be converted to an absolute profile using linear correlation with HPT data.

The probe 9 can comprise a plurality of additional sensors for measuring the soil parameters. A plurality of sensors can be arranged to generate electrical signals representative of the measured values. A multi-parameter probe can be employed for providing a tool which allows acquisition of several parameters with just one push. In an embodiment, the acquisition of one or more of the parameters can be on-the-fly or real-time. Since the measurements can be conducted simultaneously in one push, it is not necessary to carry out multiple measurements. In this way, a cost-effective method for subsurface investigation can be obtained. In prior art methods, typically a plurality of separate pushes were necessary to acquire the same amount and volume of data, usually by use of multiple separate probes.

Other sensors can be included in the probe 9 to allow e.g. an improved understanding of the spatial distribution of contaminants when investigating the soil 2 using the probe 9, which can deliver the basis for a reliable risk assessment and remediation planning of subsurface contamination. In an exemplary embodiment, a MIP-HPT-CPT (Membrane Interface Probe—Hydraulic Profiling Tool—Cone Penetration Test) probe is employed, which can provide a simultaneous detection and measurement of volatile organic compounds, soil classification, hydraulic characteristics as well as electrical conductivity and dynamic porewater pressure. In an exemplary embodiment, the probe 9 can therefore be also used to identify potential contaminant migration pathways. Similarly, it can help to identify zones for remedial material injection or provide qualitative guidance on how difficult injection may be in different zones of the formation. Further, hydraulic conductivities as well as mass flow rates can be obtained by a combined processing of the acquired datasets. In an exemplary embodiment, strain gauge load cells can be arranged on the probe for measuring forces resisting tip penetration, lateral forces resisting penetration.

In another exemplary embodiment, the method for determining soil parameters, comprising penetrating a hydraulic profiling tool (HPT) probe into a soil; carrying out a plurality of pumping tests wherein infiltration liquid is pumped into the soil from an injection port of the HPT probe at different, substantially constant, liquid injection flow rates Q; measuring, for each of the plurality of MPTs, starting from a substantially hydrostatic state, a pressure response in the soil by a pressure transducer arranged at a portion of the HPT probe, the pressure response resulting from the injection of liquid through the injection port of the HPT probe.

Further, the present invention can be carried out by modifying existing probes, such as HTP, CPT, and/or MIP probes, which are pushed into the subsurface soil to obtain data. Additionally or alternatively, the probe 9 can be detachably arranged and/or interchangeable.

In an exemplary embodiment, data acquired in the field is transferred online (e.g. wireless) and is processed by a user using one or more software packages. If for example the probe comprises a plurality of sensors, data coming from the different sensors can be processed by different software packages or a same software package. Software packages can further be arranged to communicate and work together. After processing, processed data can be displayed (e.g. 2D, 3D, quasi-3D, etc. visualization) using a visualization software package. Datasets can be visualized as 3D-blockdiagrams, 3D-stacked isomaps, cross-sections, maps of maximum signals, etc. Other visualizations are possible.

The depth of penetration L can be seen as the penetrated distance of the probe 9 through the soil surface 2a into the soil 2. In the shown embodiment of FIG. 2, the probe 9 has penetrated the soil 2 substantially perpendicular with respect to the ground or soil surface. However, other types of penetrations are possible.

Herein, the invention is described with reference to specific examples of embodiments of the invention. It will, however, be evident that various modifications and changes may be made therein, without departing from the essence of the invention. For the purpose of clarity and a concise description features are described herein as part of the same or separate examples or embodiments, however, alternative embodiments having combinations of all or some of the features described in these separate embodiments are also envisaged.

It will be appreciated that the method may include computer implemented steps. Embodiments may comprise computer apparatus, wherein processes are performed in a computer apparatus. The invention also extends to computer programs, particularly computer programs on or in a carrier, adapted for putting the invention into practice. The program may be in the form of source or object code or in any other form suitable for use in the implementation of the processes according to the invention. The carrier may be any entity or device capable of carrying the program. For example, the carrier may comprise a storage medium, such as a ROM, for example a CD ROM or a semiconductor ROM, or a magnetic recording medium, for example a floppy disc, USB memory or hard disk. Further, the carrier may be a transmissible carrier such as an electrical or optical signal which may be conveyed via electrical or optical cable or by radio or other means, e.g. via the internet or cloud.

Some embodiments may be implemented, for example, using a machine or tangible computer-readable medium or article which may store an instruction or a set of instructions that, if executed by a machine, may cause the machine to perform a method and/or operations in accordance with the embodiments. Such a machine may include, for example, any suitable processing platform, computing platform, computing device, processing device, computing system, processing system, computer, processor, or the like, and may be implemented using any suitable combination of hardware and/or software. The machine-readable medium or article may include, for example, any suitable type of memory unit, memory device, memory article, memory medium, storage device, storage article, storage medium and/or storage unit, for example, memory, removable or non-removable media, erasable or non-erasable media, writeable or re-writeable media, digital or analog media, hard disk drive, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, and the like, implemented using any suitable high-level, low-level, object-oriented, visual, compiled and/or interpreted programming language.

In various embodiments, the digital computer and/or the controller of the system 1 can communicate using wireless systems, wired systems, or a combination of both. When implemented as a wired system, the system may include components and interfaces suitable for communicating or wired communications media, such as input/output (I/O) adapters, physical connectors to connect the I/O adapter with a corresponding wired communications medium. When implemented as a wireless system, the system may include components and interfaces suitable for communicating over a wireless shared media, such as one or more antennas, transmitters, receivers, transceivers, amplifiers, filters, control logic, and so forth. An example of wireless shared media may include portions of a wireless spectrum, such as the RF spectrum and so forth. A wireless communication device may be included in order to transmit and receive signals using various suitable wireless communications techniques. Such techniques may involve communications across one or more wireless networks. Exemplary wireless networks include, but are not limited to, cellular networks, wireless local area networks (WLANs, cfr. WiFi), wireless personal area networks (WPANs), wireless metropolitan area network (WMANs), satellite networks, et cetera. In communicating across such networks, the transmitter may operate in accordance with one or more applicable standards in any version.

Herein, the invention is described with reference to specific examples of embodiments of the invention. It will, however, be evident that various modifications, variations, alternatives and changes may be made therein, without departing from the essence of the invention. For the purpose of clarity and a concise description features are described herein as part of the same or separate embodiments, however, alternative embodiments having combinations of all or some of the features described in these separate embodiments are also envisaged and understood to fall within the framework of the invention as outlined by the claims. The specifications, figures and examples are, accordingly, to be regarded in an illustrative sense rather than in a restrictive sense. The invention is intended to embrace all alternatives, modifications and variations which fall within the spirit and scope of the appended claims. Further, many of the elements that are described are functional entities that may be implemented as discrete or distributed components or in conjunction with other components, in any suitable combination and location.

In the claims, any reference signs placed between parentheses shall not be construed as limiting the claim. The word 'comprising' does not exclude the presence of other features or steps than those listed in a claim. Furthermore, the words 'a' and 'an' shall not be construed as limited to 'only one', but instead are used to mean 'at least one', and do not exclude a plurality. The mere fact that certain measures are recited in mutually different claims does not indicate that a combination of these measures cannot be used to an advantage.

The invention claimed is:

1. A method for determining soil properties, comprising:
   pushing a probe system into a soil until a predetermined depth of penetration, the probe system including at least a liquid injection port, at least one pressure transducer, and strain gauge load cells;
   while the probe system is being pushed to the predetermined depth of penetration:
   injecting an infiltration liquid through the at least one liquid injection port into the soil;
   determining, by data obtained from the strain gauge load cells, a mechanical tip resistance experienced by the probe system while the probe system is being pushed into the soil; and measuring, at the least one pressure transducer and based on the infiltration liquid, one or more first pressure responses of the soil;

halting the pushing of the probe system at the predetermined depth of penetration;

carrying out a plurality of consecutive pumping tests at the predetermined depth of penetration, without waiting between each of the plurality of consecutive pumping tests, by pumping, while the probe system is halted, the infiltration liquid through the at least one liquid injection port into the soil at a different injection rate for each of the consecutive pumping tests;

measuring, at the at least one pressure transducer and based on the pumping while the probe system is halted, one or more second pressure responses of the soil;

determining, based on the one or more first pressure responses and the one or more second pressure responses, one or more parameters of the soil, the one or more parameters of the soil including at least one of permeability and storativity; and determining, based at least in part on the determined mechanical tip resistance, information of subsurface lithology.

2. The method according to claim 1, wherein the plurality of consecutive pumping tests are carried out at a substantially fixed depth of soil penetration of the probe system.

3. The method according to claim 1, wherein the carrying out the plurality of consecutive pumping tests start from a substantially hydrostatic pressure state.

4. The method according to claim 1, further comprising carrying out at least one dissipation test, wherein pumping of infiltration liquid through the liquid injection port is stopped in order to obtain a substantially hydrostatic pressure state.

5. The method according to claim 4, wherein the at least one dissipation test is carried out prior to starting the plurality of consecutive pumping tests.

6. The method according to claim 1, wherein each successive pumping test is carried out when a pressure response during a previous pumping test has converged.

7. The method according to claim 1, wherein the plurality of consecutive pumping tests comprise a plurality of successive pumping tests, wherein a liquid injection flow rate for each successive pumping test is stepwise adjusted.

8. The method according to claim 1, wherein the liquid injection port and the at least one pressure transducer are arranged at a distance from each other.

9. The method according to claim 8, wherein the liquid injection port and the at least one pressure transducer are arranged at a distance from each other with respect to a longitudinal direction of a probe of the probe system.

10. The method according to claim 8, wherein the liquid injection port and the at least one pressure transducer are arranged at a distance from each other with respect to a lateral direction of a probe of the probe system.

11. The method according to claim 1, wherein the plurality of consecutive pumping tests include a plurality of series of pumping tests, each series of pumping tests being carried out at a different depth of penetration of the probe system.

12. The method according to claim 1, wherein the method is carried out during a cone penetration test in which the probe system is pushed into the soil at a controlled penetration rate, wherein the plurality of consecutive pumping tests are carried out with the probe system substantially stationary with respect to the soil.

13. The method according to claim 12, wherein the cone penetration test is resumed at a controlled penetration rate after carrying out the plurality of consecutive pumping tests.

14. The method according to claim 1, further comprising processing measured data from the plurality of consecutive pumping tests by fitting the measured data on a computational model in order to determine at least one of permeability and storativity.

15. The method according to claim 14, wherein the at least one of permeability and storativity is obtained by an inverse modelling on generated liquid pressure tests.

16. The method according to claim 1, further comprising determining a permeability on the basis of a ratio between a flow rate and a liquid injection induced pressure.

17. The method according to claim 1, wherein the infiltration liquid is ground water.

18. The method according to claim 1, wherein after the plurality of consecutive pumping tests have been performed at the predetermined depth of penetration, pushing the probe system further into the soil until a second predetermined depth of penetration;

determining, by data obtained from the strain gauge load cells, the mechanical tip resistance experienced by the probe system while the probe system is being pushed into the soil to the second depth of penetration;

injecting, while the probe system is being pushed into the soil until the second predetermined depth of penetration, the infiltration liquid through the at least one liquid injection port into the soil;

measuring, at the least one pressure transducer and based on the infiltration liquid, one or more third pressure responses of the soil;

halting, the pushing of the probe system at the second predetermined depth of penetration;

carrying out a plurality of second consecutive pumping tests at the predetermined second depth of penetration without waiting between the plurality of consecutive pumping tests by pumping, while the probe system is halted, the infiltration liquid through the at least one liquid injection port into the soil at a different injection rate for each of the consecutive second pumping tests;

measuring, at the at least one pressure transducer and based on the pumping while the probe system is halted, one or more fourth pressure responses of the soil.

19. The method of claim 18, wherein a continuous permeability profile of the soil is determined, by combining measurement data from the plurality of consecutive pumping tests and the plurality of second consecutive pumping tests.

20. A system for determining soil properties, comprising:

a probe system comprising at least a liquid injection port, at least one pressure transducer, and strain gauge load cells, the probe system configured to:

push into a soil until a predetermined depth of penetration;

while the probe system is being pushed to the predetermined depth of penetration:

inject an infiltration liquid through the at least one liquid injection port into the soil;

determine, by data obtained from the strain gauge load cells, a mechanical tip resistance experienced by the probe system while the probe system is being pushed into the soil; and measure, at the least one pressure transducer and based on the infiltration liquid, one or more first pressure responses of the soil;

halt the pushing of the probe system at a predetermined depth of penetration;

carry out a plurality of consecutive pumping tests at the predetermined depth of penetration, without waiting between each of the plurality of consecutive pumping tests, by pumping, while the probe system is halted, the infiltration liquid through the at least one liquid injection port into the soil at a different injection rate for each of the consecutive pumping tests;

measure, at the at least one pressure transducer and based on the pumping while the probe system is halted, one or more second pressure responses in the soil; and a digital computer configured to receive measurement data from the probe system and based on the one or more first pressure responses and the one or more second pressure responses determine one or more parameters of the soil, the one or more parameters of the soil including at least one of permeability and storativity, and, based at least in part on the determined mechanical tip resistance, determine information of subsurface lithology.

21. The system according to claim 20, further configured to carry out the plurality of consecutive pumping tests at a substantially fixed depth of soil penetration of the probe system.

22. The system according to claim 20, wherein the system is configured to push the probe system into a soil at a plurality of depths of penetration of the probe system.

23. The system according to claim 20, wherein the probe system includes a probe having a substantially elongated tubular shape comprising a tip facing in a longitudinal penetration direction of the probe and configured to penetrate the soil.

24. The system according to claim 23, wherein the liquid injection port and the at least one pressure transducer are arranged at a distance from each other with respect to a longitudinal penetration direction of the probe.

25. The system according to claim 23, wherein the liquid injection port and the at least one pressure transducer are arranged at a distance from each other with respect to a lateral direction of the probe.

26. The system according to claim 20, wherein the liquid injection port and the at least one pressure transducer are arranged at a distance from each other.

27. The system according to claim 20, further comprising a post-processing system for obtaining a continuous permeability profile of a soil by combining measurement data from the plurality of consecutive pumping tests with measurement data from a hydraulic profiling tool cone penetration test, wherein probe system is configured to push into the soil at a controlled penetration rate.

28. The system according to claim 20, wherein the system is arranged on a movable unit.

29. A non-transitory computer readable medium for determining soil properties using a probe system comprising at least one liquid injection port, at least one pressure transducer, and strain gauge load cells, which the non-transitory computer readable medium storing instructions which when executed by a processor, causes the processor to:

while the probe system is being pushed to the predetermined depth of penetration:
injecting an infiltration liquid through the at least one liquid injection port into the soil;
determine a mechanical tip resistance experienced by of the probe system by data obtained from the strain gauge load cells; and
measure, at the at least one pressure transducer and based on the infiltration liquid, a first pressure response in the soil resulting from the injection of liquid through the liquid injection port;

carry out plurality of consecutive pumping tests, while the probe system is halted at the a predetermined depth of penetration without waiting between the plurality of consecutive pumping tests, wherein the infiltration liquid is pumped through the at least one liquid injection port of the probe system at a different liquid injection flow rate for each of the consecutive pumping tests;

measure, at the at least one pressure transducer, for each of the plurality of consecutive pumping tests, a second pressure response in the soil resulting from the injection of liquid through the liquid injection port;

receive, for each of the plurality of consecutive pumping tests, measured data;

determining from the measured data information representative of soil properties, the one or more parameters of the soil including at least one of permeability and storativity; and determining, based at least in part on the mechanical tip resistance, information of subsurface lithology.

* * * * *